US012758468B2

(12) United States Patent
Hallisey et al.

(10) Patent No.: US 12,758,468 B2
(45) Date of Patent: Oct. 13, 2026

(54) VACUUM DRAINAGE COLLECTION BOTTLE WITH VACUUM INDICATOR

(71) Applicant: Merit Medical Systems, Inc., South Jordan, UT (US)

(72) Inventors: Michael Hallisey, Salem, SC (US); Chad Yates, Lehi, UT (US); Jonathan Cheney, West Jordan, UT (US); Michael Dean Haslam, Sandy, UT (US); Richard P. Jenkins, Bluffdale, UT (US); Kenneth Sykes, Bluffdale, UT (US); Gregory R. McArthur, Sandy, UT (US); Jim Mottola, West Jordan, UT (US); Fred Lampropoulos, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 17/657,088

(22) Filed: Mar. 29, 2022

(65) Prior Publication Data

US 2022/0313552 A1 Oct. 6, 2022

Related U.S. Application Data

(60) Provisional application No. 63/231,135, filed on Aug. 9, 2021, provisional application No. 63/188,789, filed (Continued)

(51) Int. Cl.

| | |
|---|---|
| ***A61J 1/14*** | (2023.01) |
| ***A61F 13/05*** | (2024.01) |

(52) U.S. Cl.

CPC ............. *A61J 1/1418* (2015.05); *A61F 13/05* (2024.01)

(58) Field of Classification Search

CPC . A61J 1/1418; A61F 13/00068; A61M 1/732; A61M 1/66

See application file for complete search history.

(56) References Cited

U.S. PATENT DOCUMENTS

| | | | |
|---|---|---|---|
| 2,672,141 | A | 3/1954 | Filger |
| D202,299 | S | 9/1965 | Karr et al. |

(Continued)

FOREIGN PATENT DOCUMENTS

| | | |
|---|---|---|
| CN | 205031619 | 2/2016 |
| EP | 0381123 A1 | 8/1990 |

(Continued)

OTHER PUBLICATIONS

International Search Report and Written Opinion dated Jan. 3, 2022 for PCT/US2021/050132.

(Continued)

*Primary Examiner* — Rebecca E Eisenberg
*Assistant Examiner* — Katherine-Ph Minh Pham
(74) *Attorney, Agent, or Firm* — Dorsey & Whitney LLP

(57) ABSTRACT

Devices, systems, and methods used to drain a body cavity under a vacuum are disclosed. The devices include a vacuum container, a cap, and a vacuum indicator. The vacuum indicator is configured to indicate a vacuum status of the container. The vacuum indicator includes one or more of an expandable member, a flexible membrane, a linear pressure gauge, a digital pressure gauge, a retractable member, a vacuum gauge, a displaceable seal member, a deflectable membrane, or a deflectable member.

16 Claims, 20 Drawing Sheets

Related U.S. Application Data on May 14, 2021, provisional application No. 63/168,024, filed on Mar. 30, 2021.

(56) References Cited

U.S. PATENT DOCUMENTS

| | | | | |
|---|---|---|---|---|
| 3,334,628 | A | 8/1967 | Saemann et al. | |
| 3,376,991 | A | 4/1968 | Deaver | |
| 3,690,497 | A * | 9/1972 | Lecinski, Jr. | B65D 41/0457 215/334 |
| 3,696,675 | A | 10/1972 | Gilmour | |
| 3,833,000 | A | 9/1974 | Bridgman | |
| 3,939,835 | A | 2/1976 | Bridgman | |
| 3,946,739 | A | 3/1976 | Berman et al. | |
| 4,063,556 | A * | 12/1977 | Thomas | A61M 1/66 116/270 |
| 4,178,932 | A | 12/1979 | Ryder et al. | |
| 4,376,439 | A * | 3/1983 | Lauterjung | A61M 1/66 600/573 |
| D280,707 | S | 9/1985 | Manishi | |
| D291,179 | S | 8/1987 | Frizon | |
| 4,820,284 | A * | 4/1989 | Hauri | A61M 1/732 604/318 |
| 4,852,753 | A * | 8/1989 | Ochs | B65D 51/145 215/271 |
| 4,944,724 | A * | 7/1990 | Goldberg | A61B 17/3401 604/323 |
| 5,078,704 | A | 1/1992 | Wejnar | |
| 5,246,142 | A | 9/1993 | Dipalma et al. | |
| D375,559 | S | 11/1996 | Baxter | |
| 5,803,282 | A | 9/1998 | Chen et al. | |
| 5,921,419 | A * | 7/1999 | Niedospial, Jr | B65D 51/002 215/247 |
| 5,938,086 | A * | 8/1999 | Gross | B65D 47/2031 222/506 |
| D423,360 | S | 4/2000 | Togasawa et al. | |
| 6,056,730 | A | 5/2000 | Greter | |
| 6,260,414 | B1 | 7/2001 | Brown et al. | |
| D449,228 | S | 10/2001 | Nosella | |
| 6,499,617 | B1 * | 12/2002 | Niedospial, Jr. | A61J 1/1481 604/905 |
| 7,048,724 | B2 | 5/2006 | Grossman et al. | |
| D547,197 | S | 7/2007 | Hermel | |
| D557,606 | S | 12/2007 | Rashid | |
| D610,019 | S | 2/2010 | Navarro et al. | |
| D632,576 | S | 2/2011 | Hermel | |
| D702,556 | S | 4/2014 | Quasters | |
| D703,058 | S | 4/2014 | Baschmakoff et al. | |
| D747,967 | S | 1/2016 | Domènech | |
| D763,699 | S | 8/2016 | Rasgon | |
| D763,700 | S | 8/2016 | Rasgon | |
| D809,391 | S | 2/2018 | Funk | |
| D833,874 | S | 11/2018 | Harrison et al. | |
| D948,708 | S | 4/2022 | Zhang | |
| 2002/0088131 | A1 | 7/2002 | Baxa et al. | |
| 2003/0139751 | A1 | 7/2003 | Evans et al. | |
| 2007/0203463 | A1 | 8/2007 | Salvadori et al. | |
| 2009/0062766 | A1 | 3/2009 | Howlett et al. | |
| 2009/0110777 | A1 | 4/2009 | Buisson | |
| 2010/0049134 | A1 | 2/2010 | Schuman, Jr. | |
| 2010/0181276 | A1 | 7/2010 | Brown et al. | |
| 2011/0303670 | A1 | 12/2011 | Baker | |
| 2012/0000878 | A1 | 1/2012 | Reisig | |
| 2013/0233822 | A1 | 9/2013 | Aneas | |
| 2014/0243707 | A1 | 8/2014 | Kerr | |
| 2015/0065969 | A1 | 3/2015 | Stinson | |
| 2015/0073387 | A1 | 3/2015 | Bushnell | |
| 2021/0009302 | A1 | 1/2021 | Kim | |
| 2022/0008650 | A1 | 1/2022 | Arinobe et al. | |
| 2022/0080097 | A1 | 3/2022 | Davis et al. | |
| 2024/0016993 | A1 | 1/2024 | Haslam et al. | |

FOREIGN PATENT DOCUMENTS

| | | | |
|---|---|---|---|
| EP | 2961446 | B1 | 9/2019 |
| KR | 1020220063545 | | 5/2022 |
| WO | 2004056408 | | 7/2004 |
| WO | 2020008067 | A1 | 1/2020 |

OTHER PUBLICATIONS

Notice of Allowance dated Oct. 19, 2022 for U.S. Appl. No. 29/776,580.

Office Action dated Feb. 16, 2023 for U.S. Appl. No. 17/473,771.

Office Action dated Jul. 11, 2022 for U.S. Appl. No. 29/776,580.

"Serifinity; B. Braun Interventional Accel Spin-Lock Connection Set—470190", www.serifinitymedical.com/products/accel-spin-lock-connection-set-b-braun-inverventional-470190-929628?variant=3077122872139 Accessed Oct. 12, 2020.

"Ward-System", Online, publication date unknown. Retrieved on Jun. 26, 2022 from URL: https://www.pfmmedical.con/productcatagogue/high_vacuum_drainage/ward_system/index.html.

Office Action dated Sep. 14, 2023 for U.S. Appl. No. 17/473,771.

International Search Report and Written Opinion dated Jul. 15, 2022 for PCT/US2022/022394.

International Search Report and Written Opinion dated Nov. 1, 2023 for PTC/US2023/069885.

Office Action dated Feb. 1, 2024 for U.S. Appl. No. 17/473,771.

European Search Report dated Jan. 16, 2025 for EP22782043.8.

Notice of Allowance dated Jan. 2, 2024 for U.S. Appl. No. 17/473,771.

Office Action dated Aug. 12, 2024 for U.S. Appl. No. 17/473,771.

Office Action dated Jul. 28, 2025 for U.S. Appl. No. 18/349,545.

Extended European Search Report dated Jun. 19, 2026 for EP23840430.5.

* cited by examiner

VACUUM DRAINAGE COLLECTION BOTTLE WITH VACUUM INDICATOR

RELATED APPLICATIONS

This application claims priority to U.S. Provisional Application No. 63/231,135, filed on Aug. 9, 2021 and titled "Vacuum Drainage Collection Bottle With Vacuum Indicator," and to U.S. Provisional Application No. 63/188,789, filed on May 14, 2021 and titled "Vacuum Drainage Collection Bottle With Vacuum Indicator," and to U.S. Provisional Application No. 63/168,024, filed on Mar. 30, 2021 and titled "Vacuum Drainage Collection Bottle With Vacuum Indicator," the disclosure of each of which is incorporated herein by reference in its entirety.

TECHNICAL FIELD

The present disclosure relates generally to devices used to drain a cavity of a patient, particularly in medical devices. More specifically, the present disclosure relates to vacuum drainage bottles.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
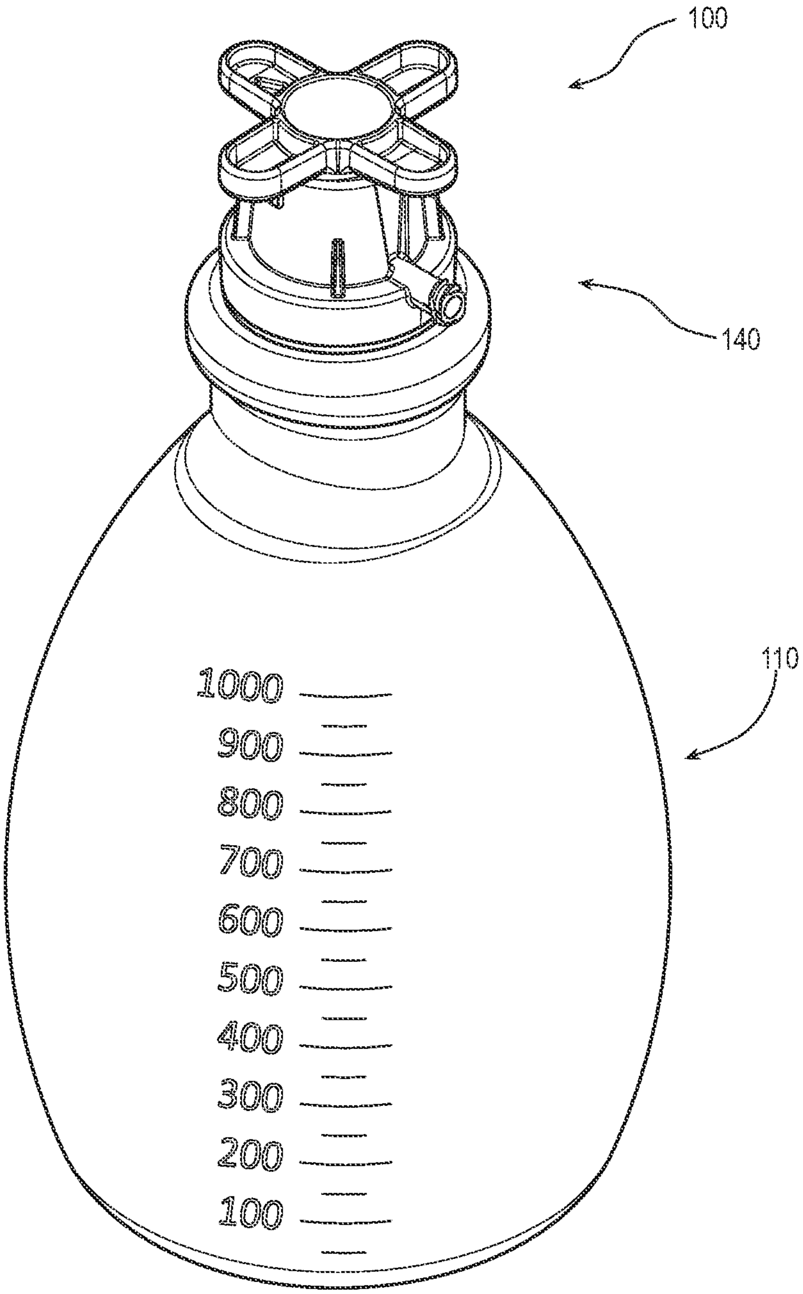
FIG. 1 is a top perspective view of an embodiment of a vacuum drainage collection bottle.

In some instances, body fluids may need to be withdrawn from a patient in the course of medical treatment. For example, two medical procedures requiring fluid removal are thoracentesis and paracentesis. In paracentesis, peritoneal fluid is aspirated from the abdomen. In thoracentesis, pleural fluid is aspirated from the thoracic cavity. In certain instances, paracentesis and thoracentesis have been observed to provide quick and effective relief with few adverse side effects. Relatively large volumes of fluid, such as five liters, may be withdrawn from a patient during a single procedure. The paracentesis and thoracentesis procedures can be conducted in a health care facility by health care workers or in a patient's home by the patient. Many existing devices are capable of performing paracentesis and thoracentesis. At its simplest, a paracentesis or thoracentesis device need only include a hollow needle with one end inserted into the patient and the other end attached to a negative gauge pressure or vacuum device, such as a vacuum drainage collection bottle.

A vacuum drainage collection bottle of the present disclosure includes a truncated football-shaped container that is provided to a user with an internal negative pressure (which can also be referred to as a negative gauge pressure) or vacuum. In certain embodiments within the scope of this disclosure, a cap may be connected to the container. The cap can have a body with an inlet in fluid communication with the container. In some embodiments, the inlet may include an external connector for connection of a drainage tube. Caps within the scope of this disclosure can include internal threads that are configured to engage with external threads of a plunger of a sealing member. In certain embodiments, the sealing member may include a stopper that selectively seals the inlet to prevent passage of fluid or gas through the inlet. The stopper may be displaced from a closed state to an open state by threadingly rotating the plunger with a plunger handle. In the open state the stopper may be displaced away from the inlet such that fluid is drawn into the container by the vacuum or negative gauge pressure within the container.

In some embodiments within the scope of this disclosure, a vacuum indicator configured to indicate the vacuum or negative gauge pressure within the container is coupled to a vacuum drainage collection bottle. The vacuum indicator can include one or more of an expandable member, a flexible membrane, a linear pressure gauge, a digital pressure gauge, a retractable member, a vacuum gauge, a displaceable seal member, a deflectable membrane, and a deflectable member. The vacuum indicator is in an activated state when the container includes the vacuum and in a non-activated state when the vacuum is depleted from the container. When the vacuum indicator is in the activated state a drainage procedure may be initiated and when the vacuum indicator is in the non-activated state the drainage procedure may be discontinued.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

FIGS. 1-18D illustrate different views of various embodiments of a vacuum drainage collection bottle and related components. In certain views the vacuum drainage collection bottle may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

Figure 2:
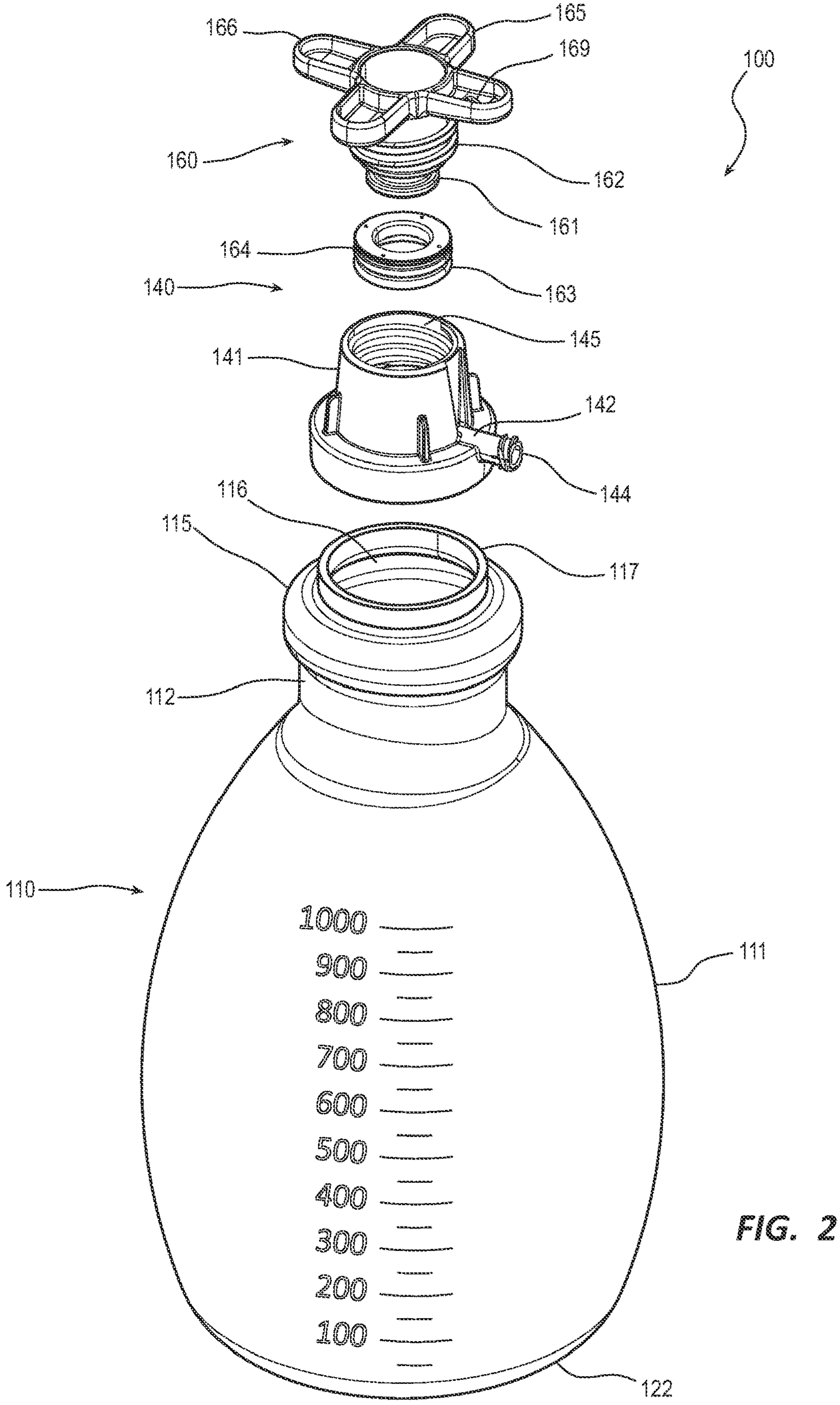
FIG. 2 is an exploded perspective view of the vacuum drainage collection bottle embodiment of FIG. 1.
Figure 3A:
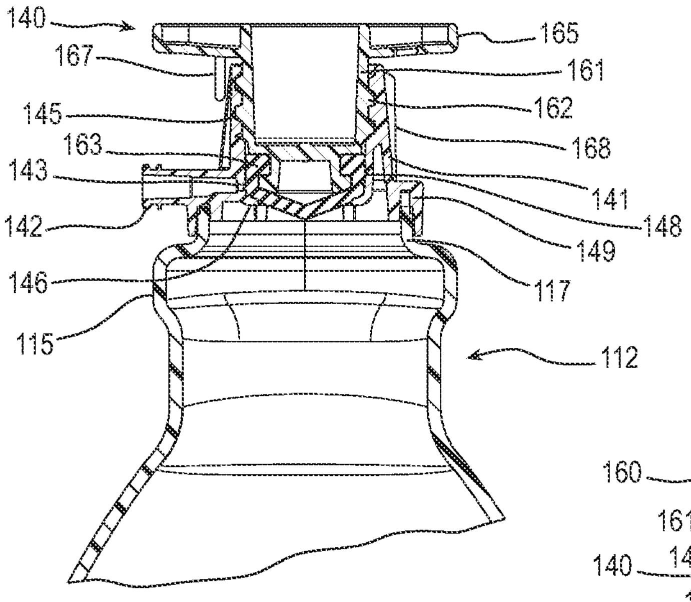
FIG. 3A is a longitudinal cross-sectional view of a cap of the vacuum drainage collection bottle embodiment of FIG. 1 in a closed state.
Figure 3B:
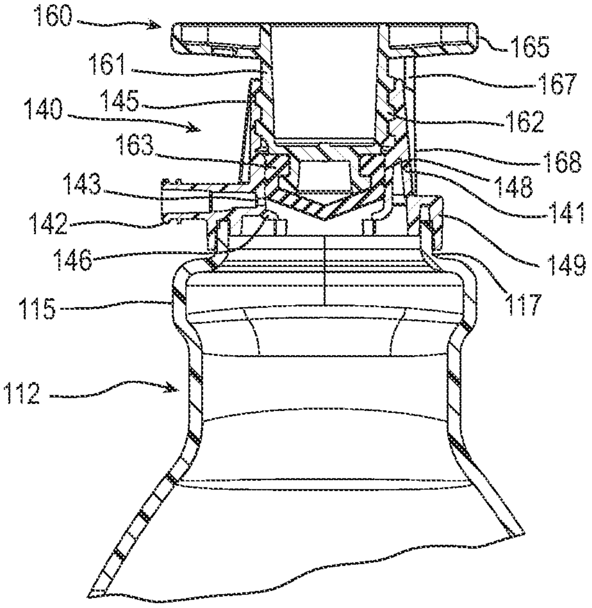
FIG. 3B is a longitudinal cross-sectional view of the cap of the vacuum drainage collection bottle embodiment of FIG. 1 in an open state.
Figure 3C:
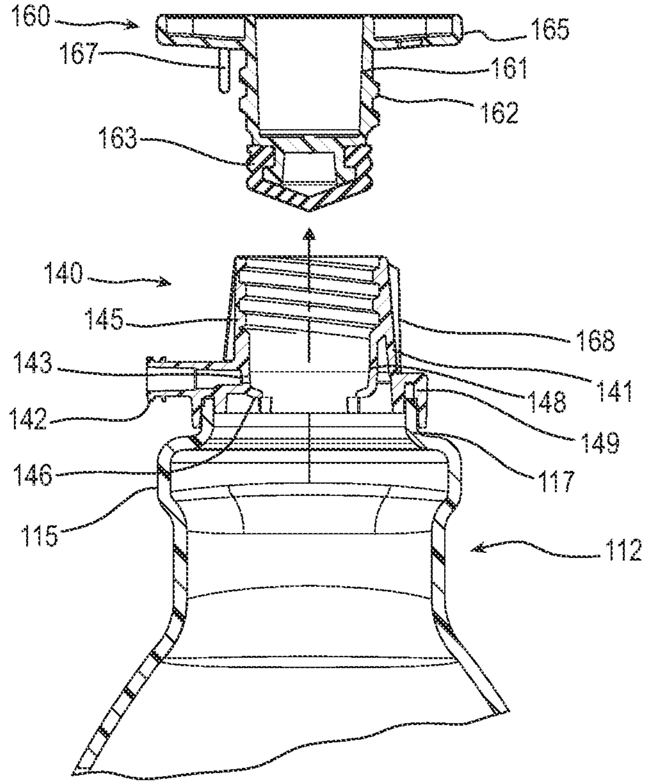
FIG. 3C is a longitudinal cross-sectional view of the cap of the vacuum drainage collection bottle embodiment of FIG. 1 with a sealing member removed from the cap.
Figure 4A:
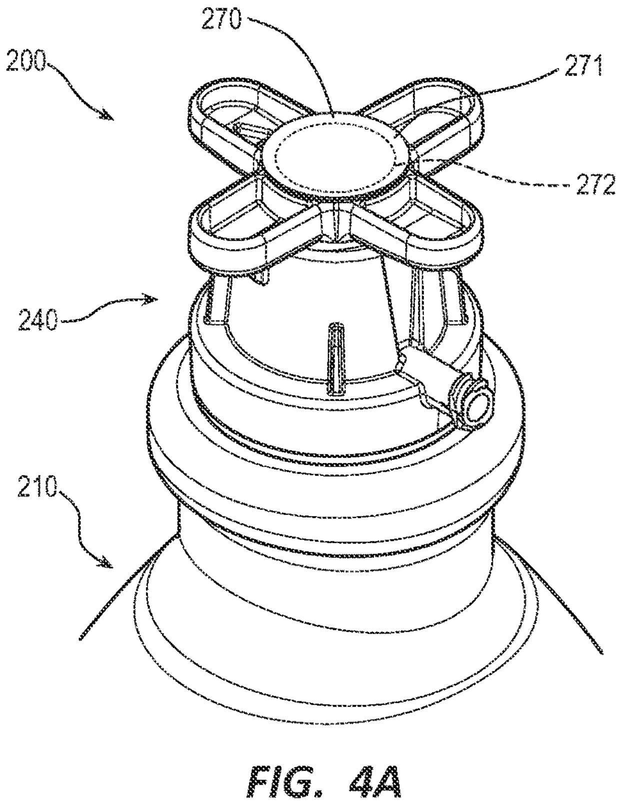
FIG. 4A is a perspective view of a portion of another embodiment of a vacuum drainage collection bottle including an elastic membrane vacuum indicator.
Figure 4B:
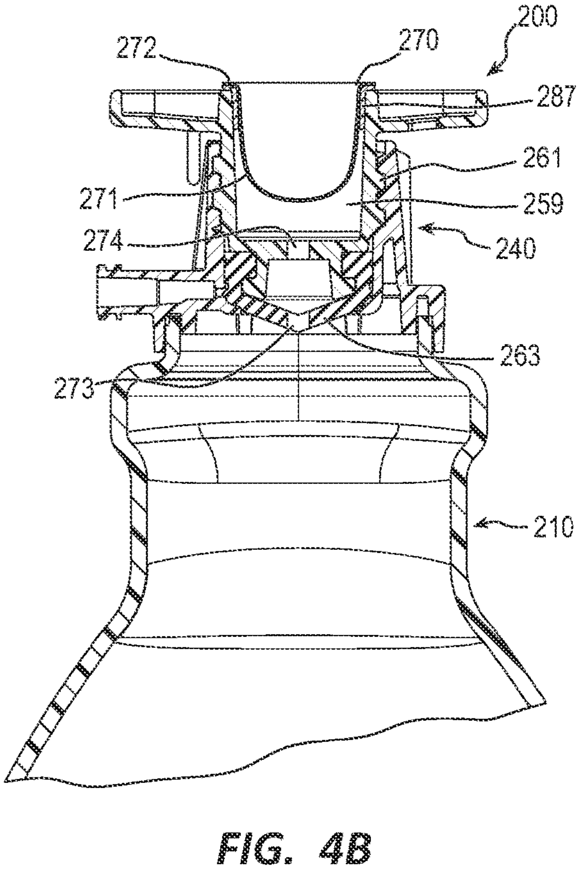
FIG. 4B is a longitudinal cross-sectional view of the portion of the vacuum drainage collection bottle of FIG. 4A with the vacuum indicator in an activated state.
Figure 4C:
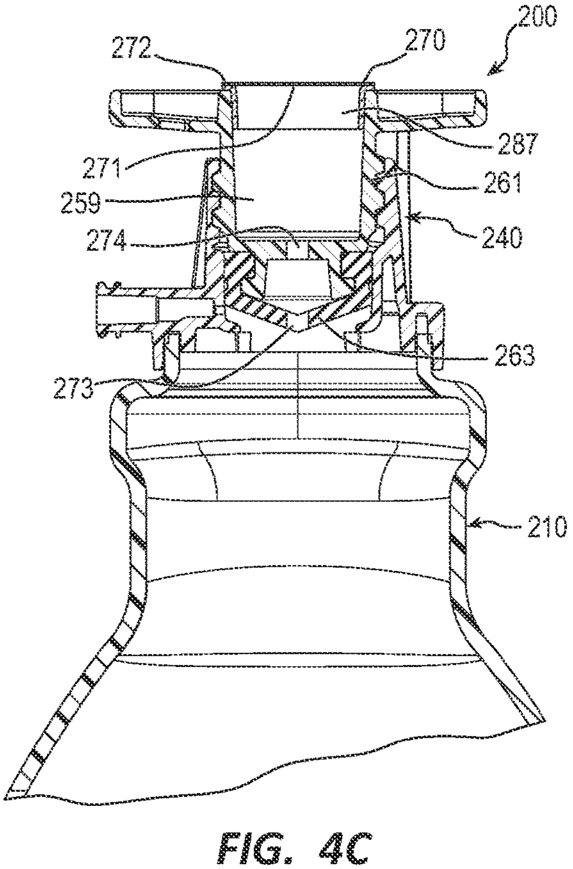
FIG. 4C is a longitudinal cross-sectional view of the portion of the vacuum drainage collection bottle of FIG. 4A with the vacuum indicator in a non-activated state.
Figure 5A:
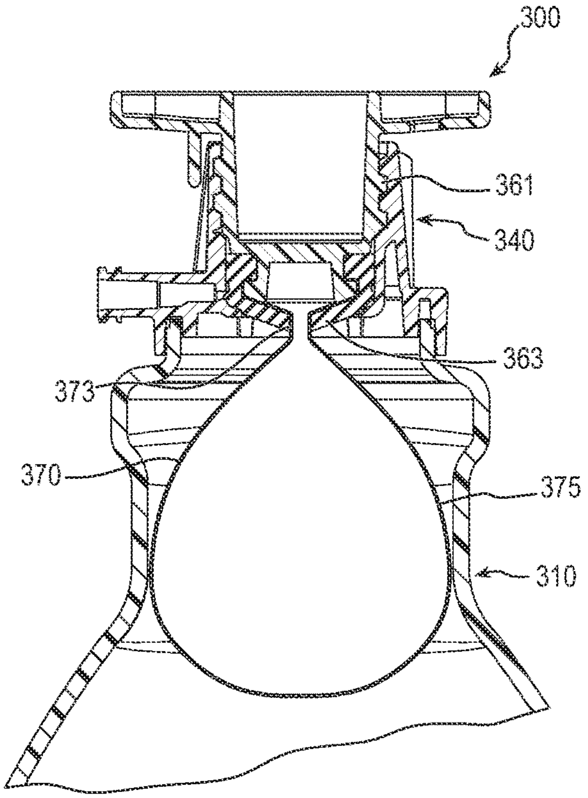
FIG. 5A is a longitudinal cross-sectional view of a portion of another embodiment of a vacuum drainage collection bottle with an expandable vacuum indicator in an activated state.
Figure 5B:
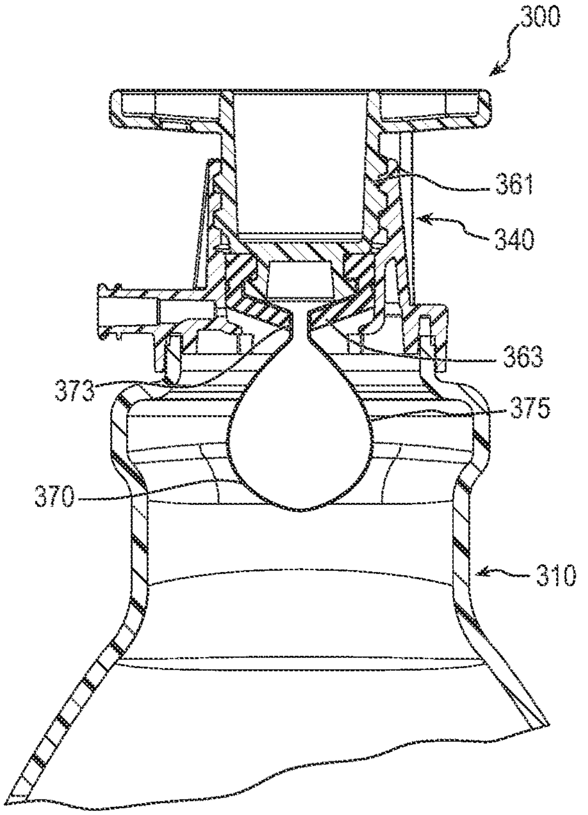
FIG. 5B is a longitudinal cross-sectional view of the portion of the vacuum drainage collection bottle of FIG. 5A with the expandable vacuum indicator in a non-activated state.
Figure 6A:
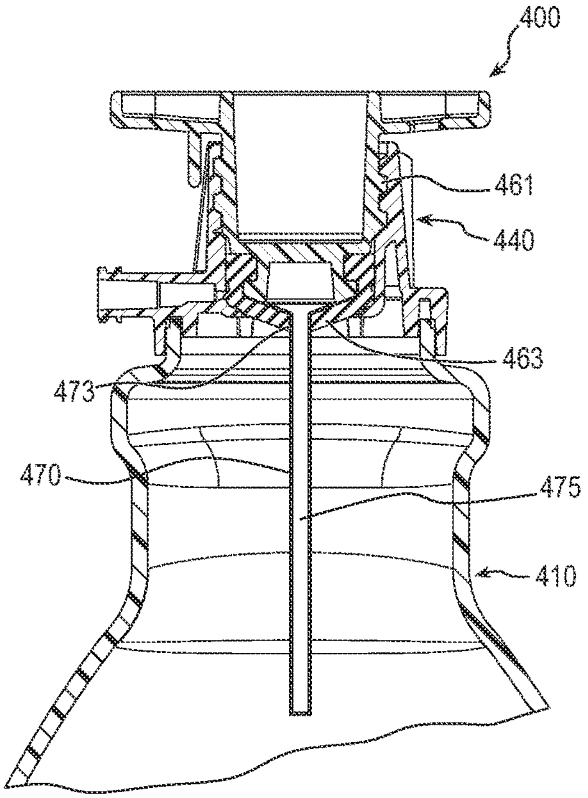
FIG. 6A is a longitudinal cross-sectional view of a portion of another embodiment of a vacuum drainage collection bottle with an expandable vacuum indicator in an activated state.
Figure 6B:
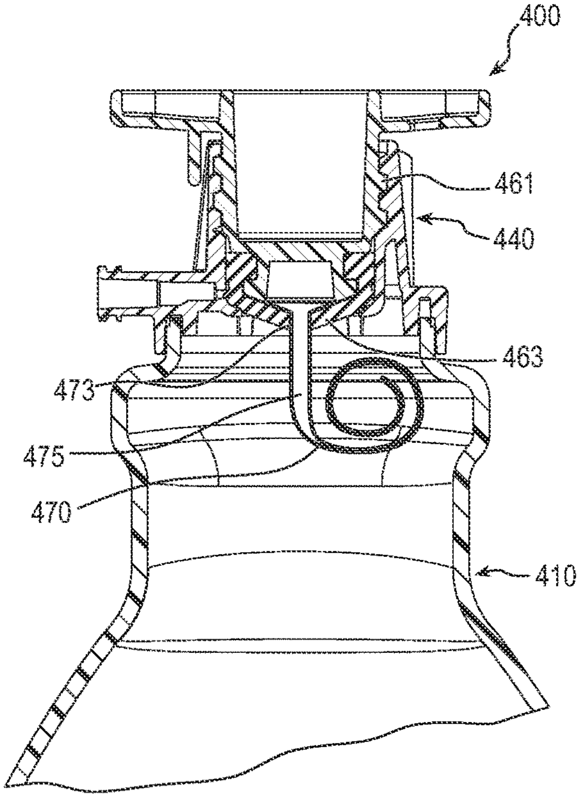
FIG. 6B is a longitudinal cross-sectional view of the portion of the vacuum drainage collection bottle of FIG. 6A with the expandable vacuum indicator in a non-activated state.
Figure 7A:
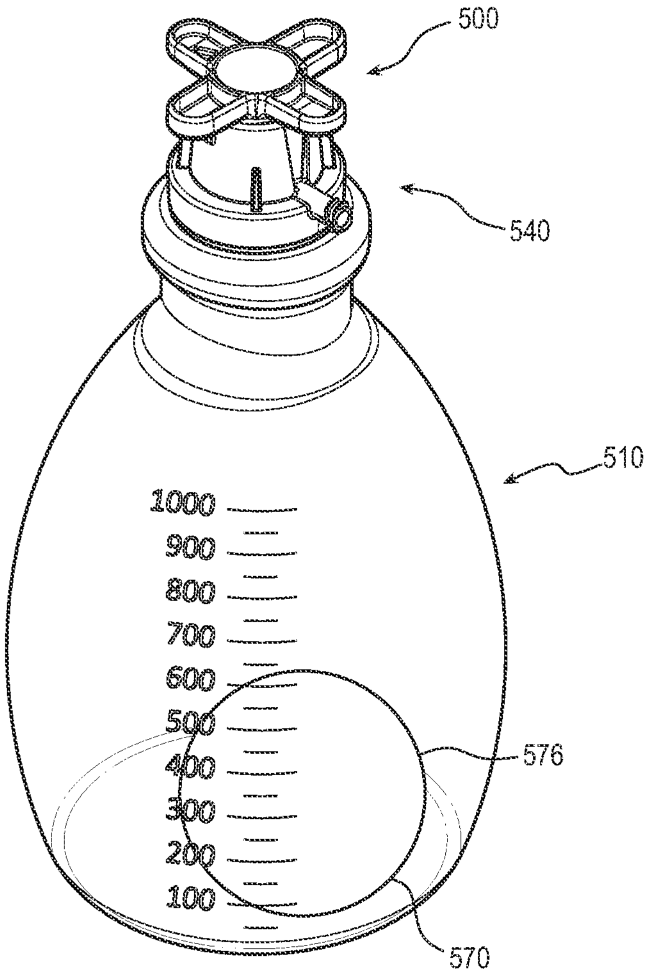
FIG. 7A is a perspective view of another embodiment of a vacuum drainage collection bottle with an expandable vacuum indicator in an activated state.
Figure 7B:
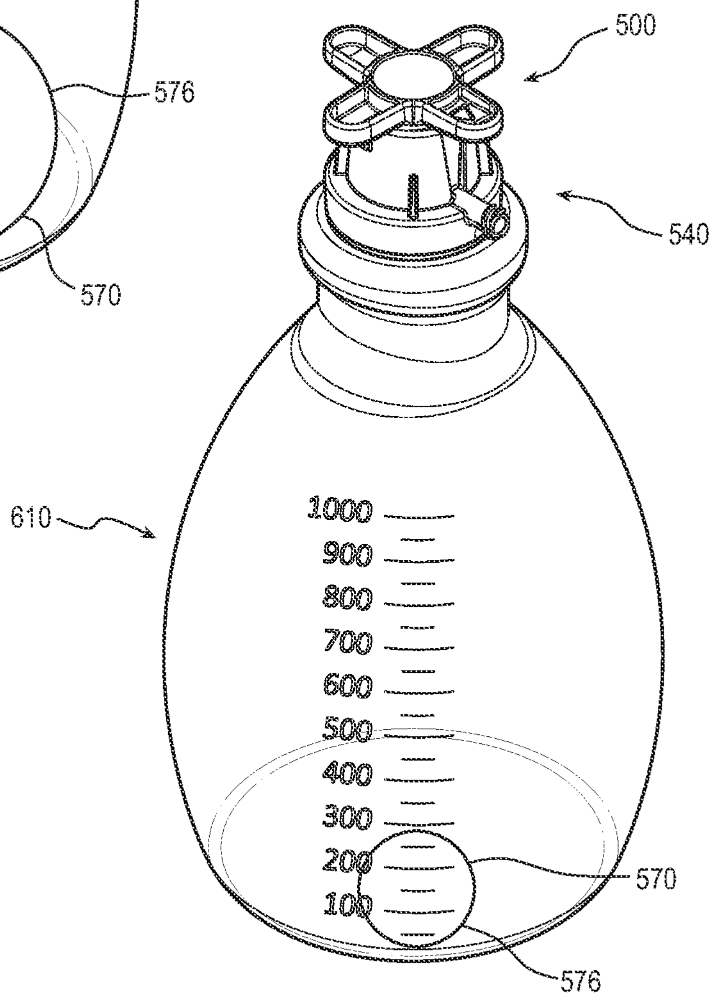
FIG. 7B is a perspective view of the vacuum drainage collection bottle of FIG. 7A with the expandable vacuum indicator in a non-activated state.
Figure 8A:
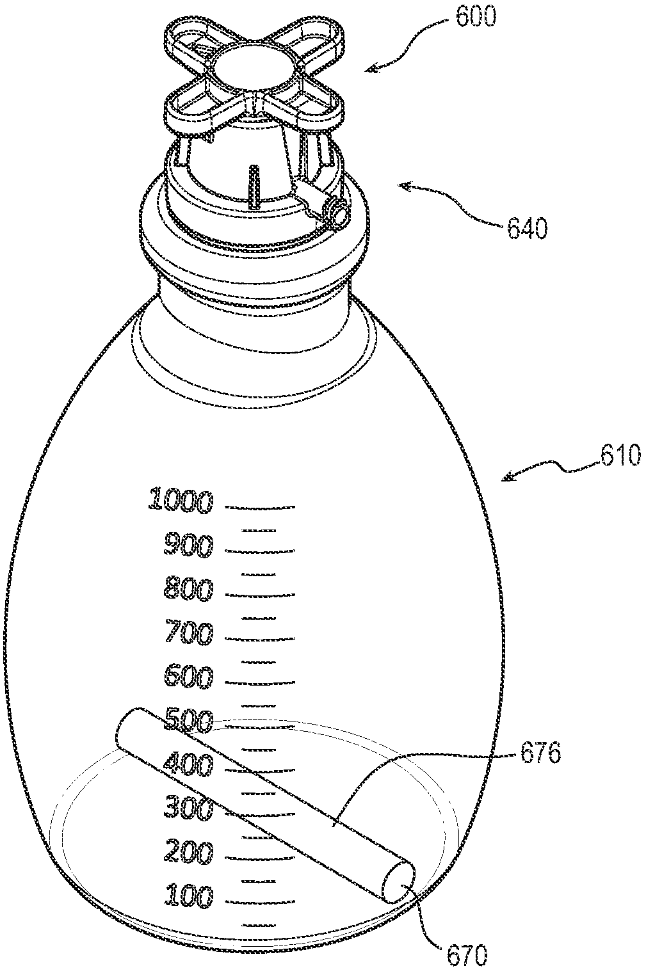
FIG. 8A is a perspective view of another embodiment of a vacuum drainage collection bottle with an expandable vacuum indicator in an activated state.
Figure 8B:
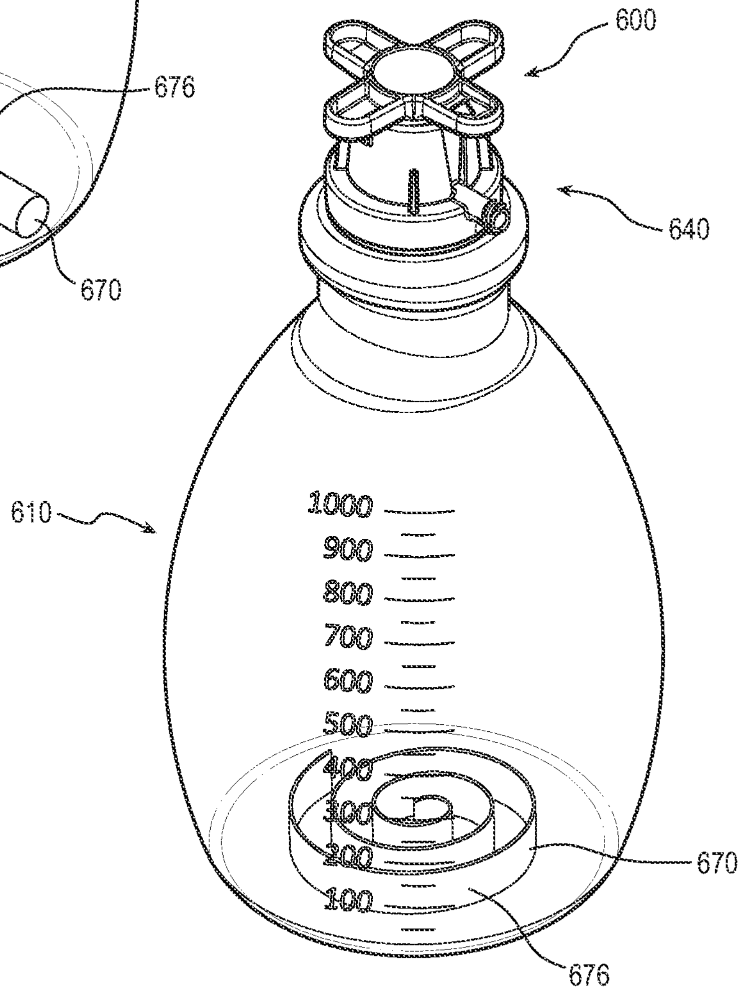
FIG. 8B is a perspective view of the vacuum drainage collection bottle of FIG. 8A with the expandable vacuum indicator in a non-activated state.
Figure 9A:
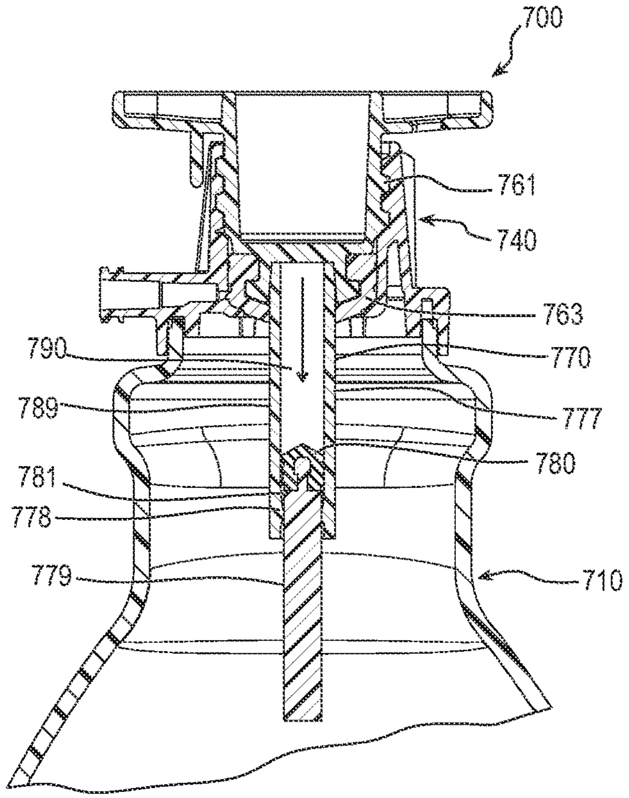
FIG. 9A is a longitudinal cross-sectional view of a portion of another embodiment of a vacuum drainage collection bottle with a linear vacuum indicator in an activated state.
Figure 9B:
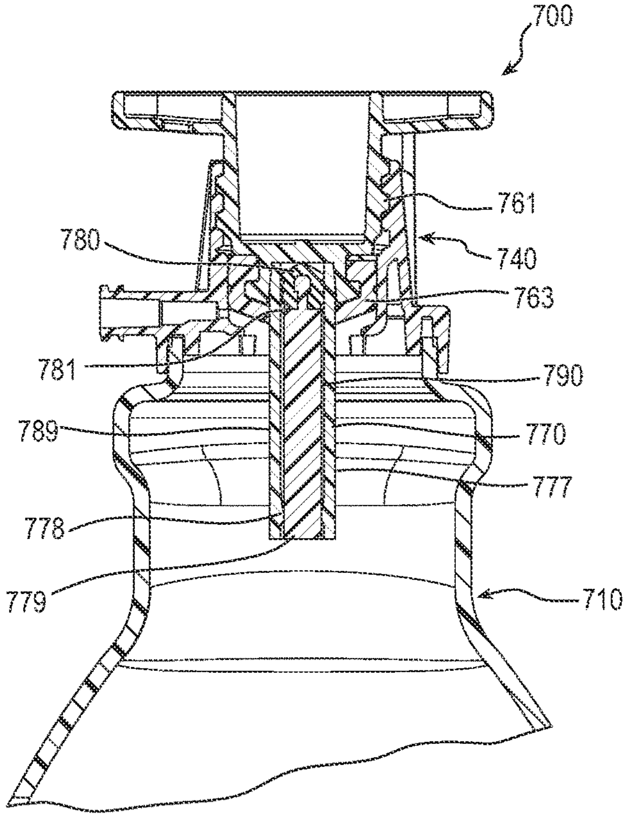
FIG. 9B is a longitudinal cross-sectional view of the portion of the vacuum drainage collection bottle of FIG. 9A with the linear vacuum indicator in a non-activated state.
Figure 10A:
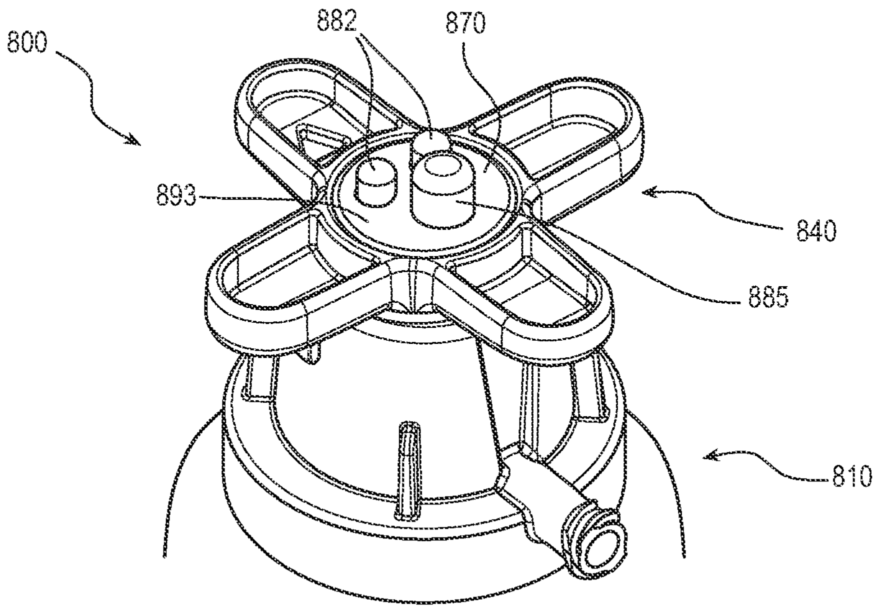
FIG. 10A is a perspective view of a portion of another embodiment of a vacuum drainage collection bottle including a digital pressure sensor vacuum indicator.
Figure 10B:
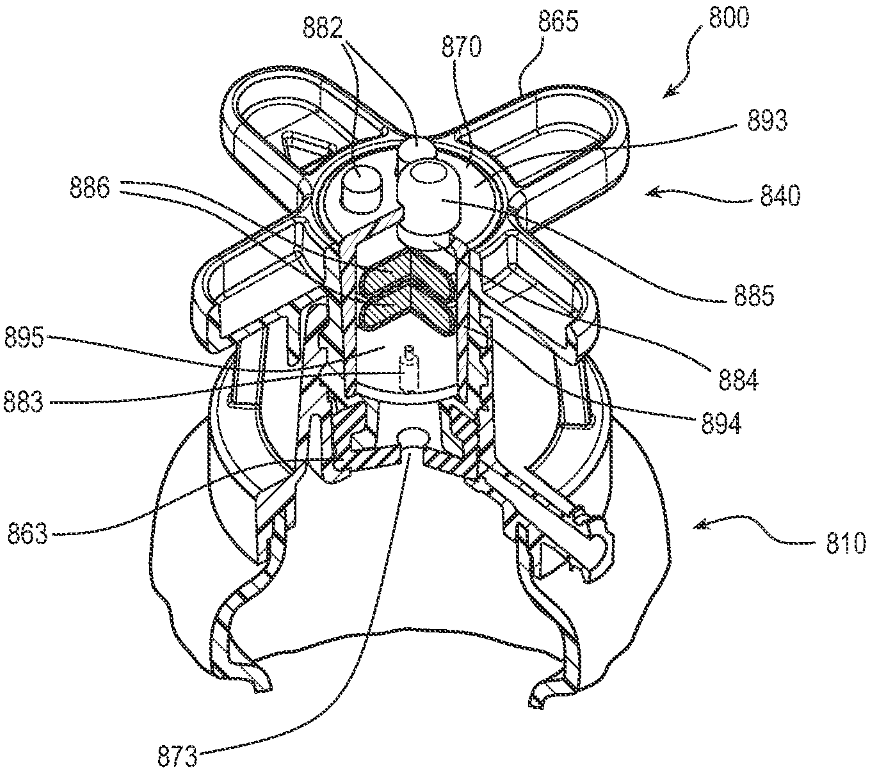
FIG. 10B is a partial longitudinal cross-sectional view of the portion of the vacuum drainage collection bottle of FIG. 10A including the digital pressure sensor vacuum indicator.
Figure 11A:
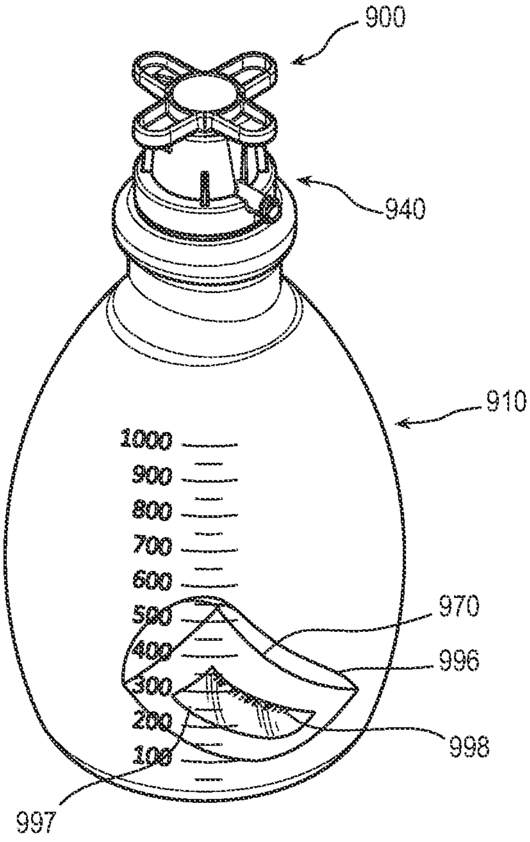
FIG. 11A is a perspective view of another embodiment of a vacuum drainage collection bottle with an expandable vacuum indicator in an activated state.
Figure 11B:
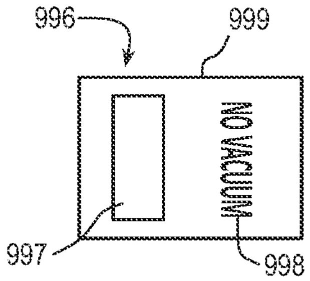
FIG. 11B is a top view of an expandable member of the expandable vacuum indicator of FIG. 11A.
Figure 11C:
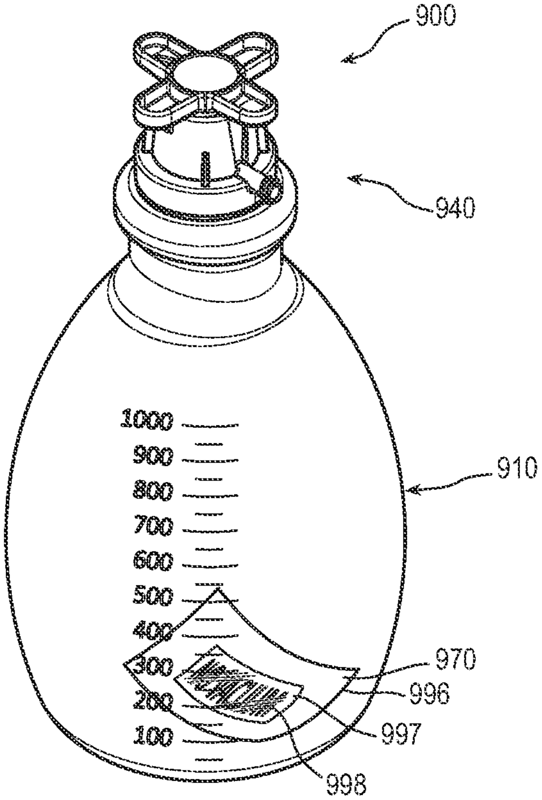
FIG. 11C is a perspective view of the vacuum drainage collection bottle of FIG. 11A with the expandable vacuum indicator in a non-activated state.
Figure 12A:
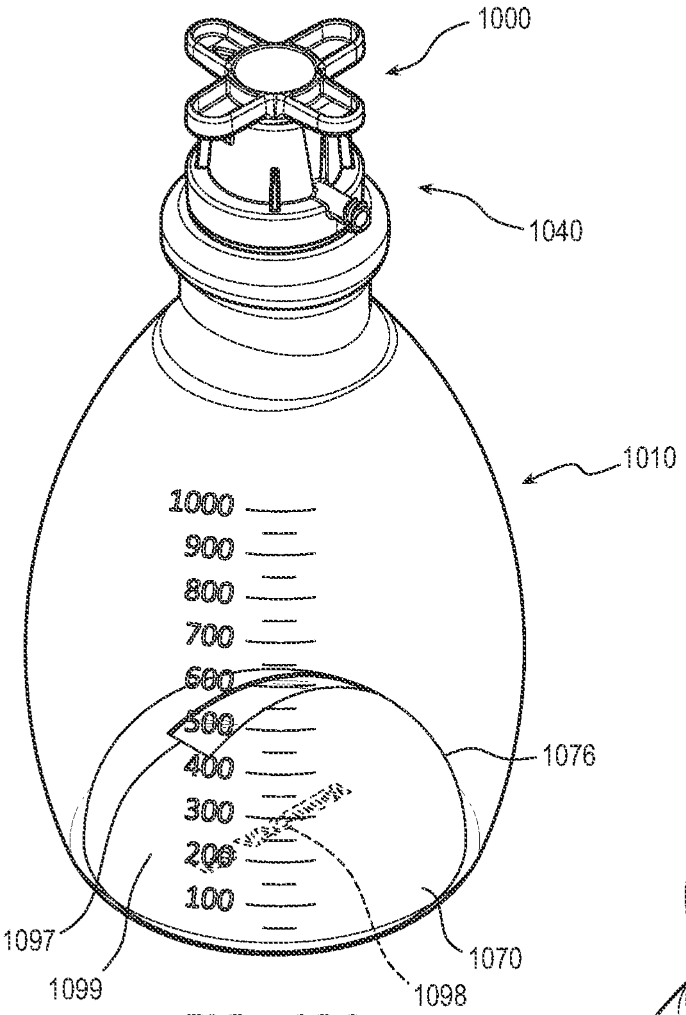
FIG. 12A is a perspective view of another embodiment of a vacuum drainage collection bottle with an expandable vacuum indicator in an activated state.
Figure 12B:
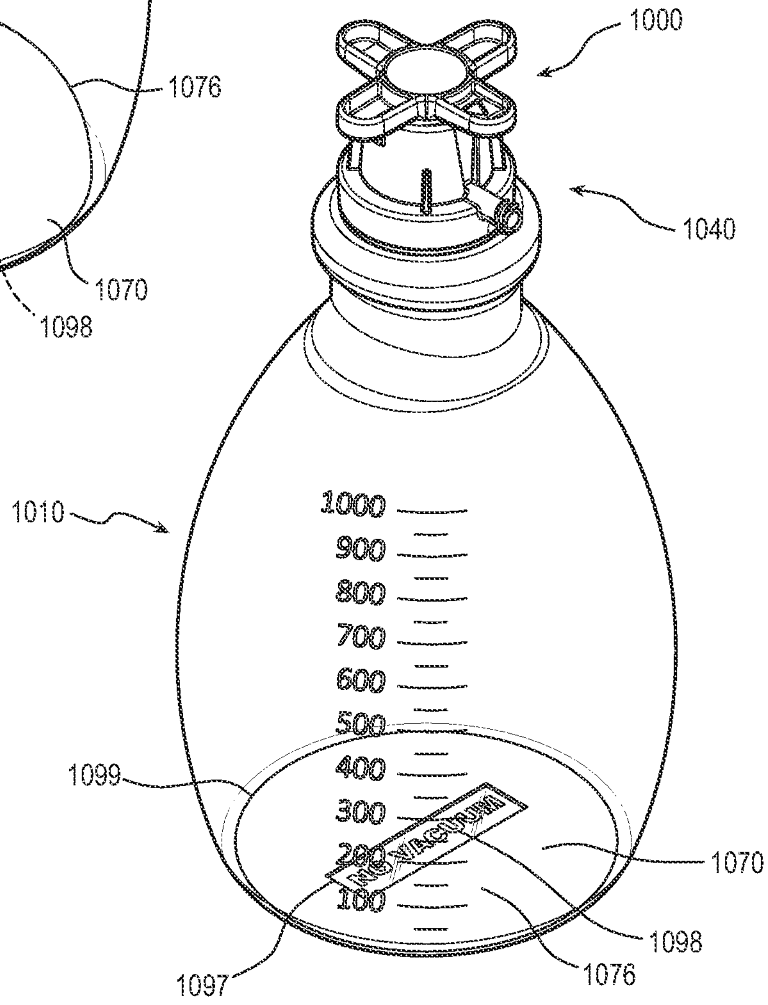
FIG. 12B is a perspective view of the vacuum drainage collection bottle of FIG. 12A with the expandable vacuum indicator in a non-activated state.
Figure 13A:
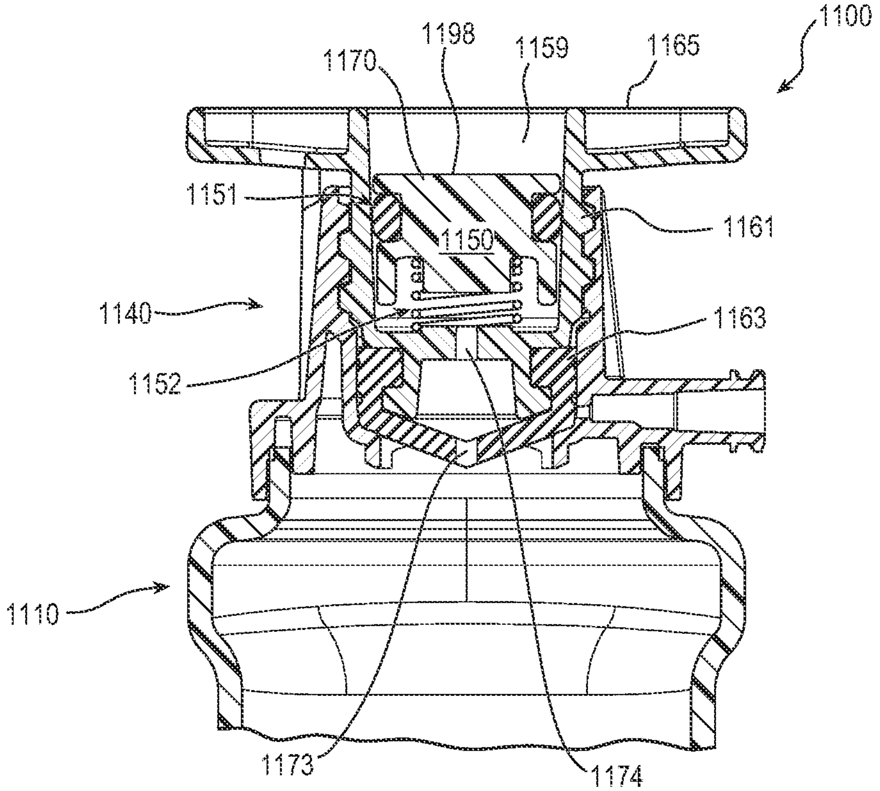
FIG. 13A is a longitudinal cross-sectional view of a portion of another embodiment of a vacuum drainage collection bottle with a retractable adapter vacuum indicator in an activated state.
Figure 13B:
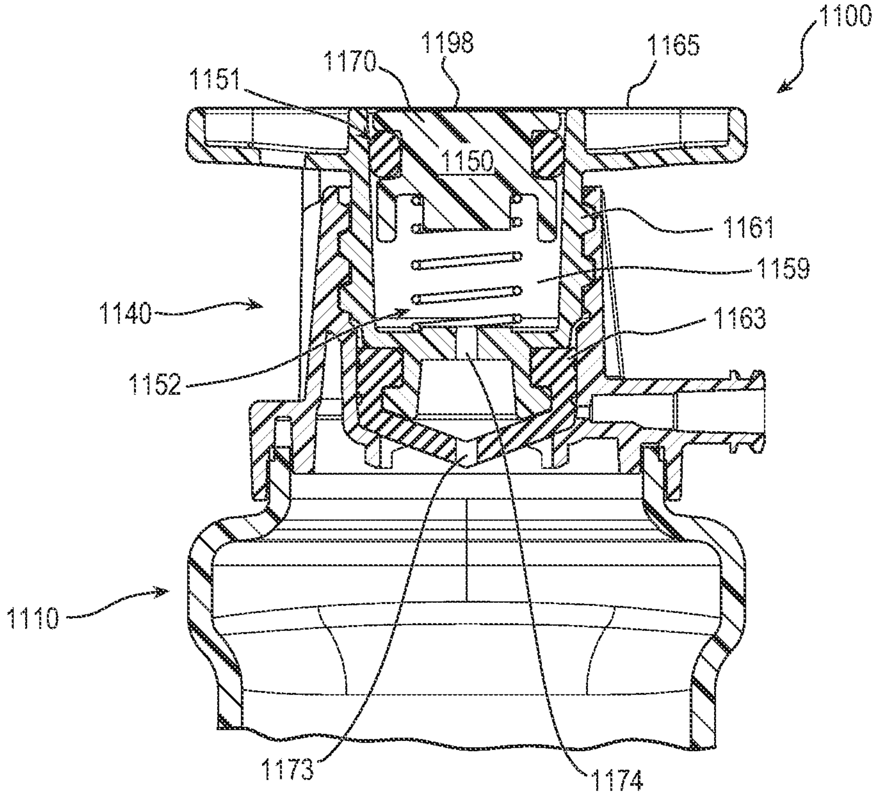
FIG. 13B is a longitudinal cross-sectional view of the portion of the vacuum drainage collection bottle of FIG. 13A with the retractable adapter vacuum indicator in a non-activated state.
Figure 14:
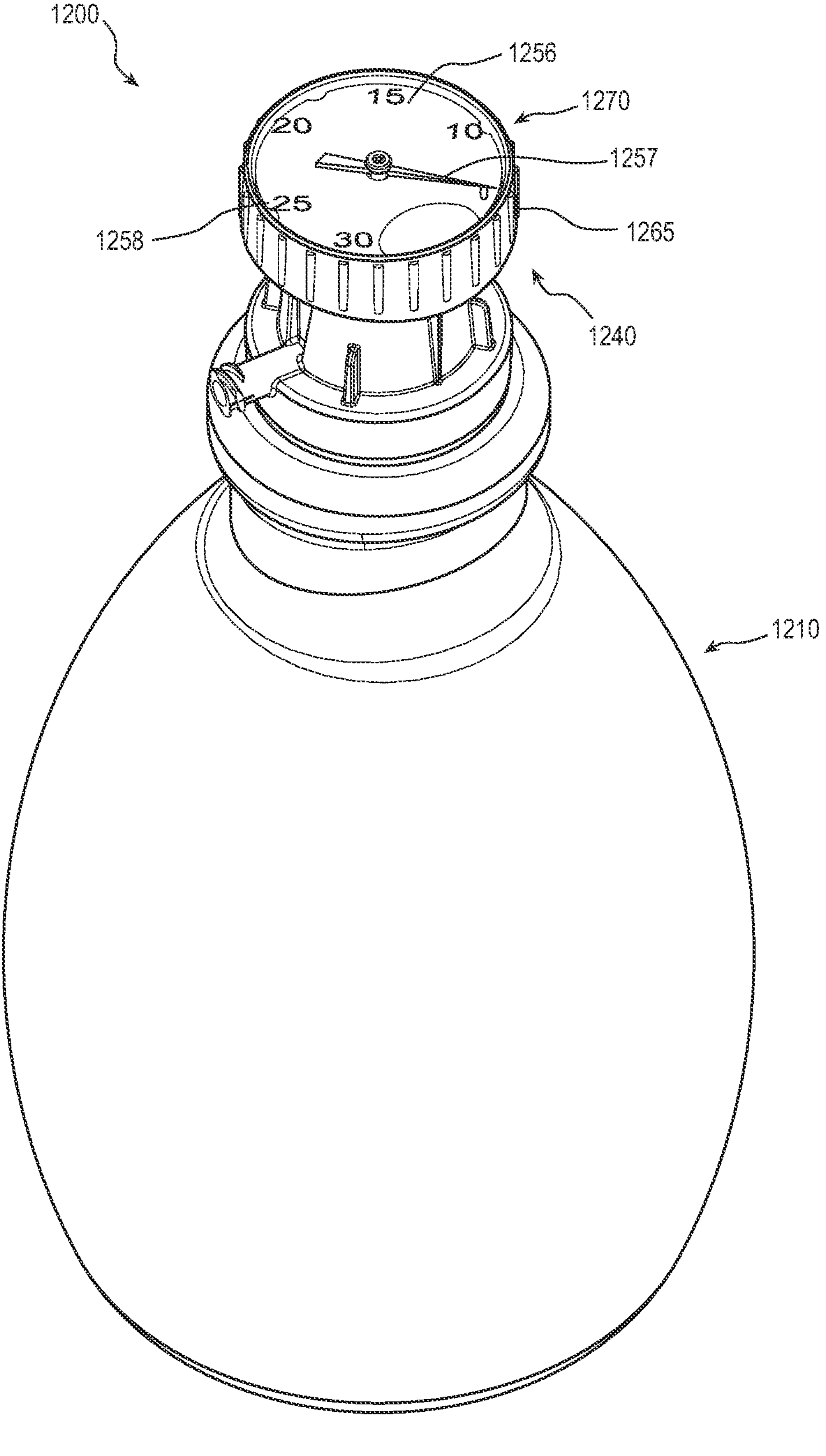
FIG. 14 is a perspective view of another embodiment of a vacuum drainage collection bottle with a vacuum gauge vacuum indicator.
Figure 15A:
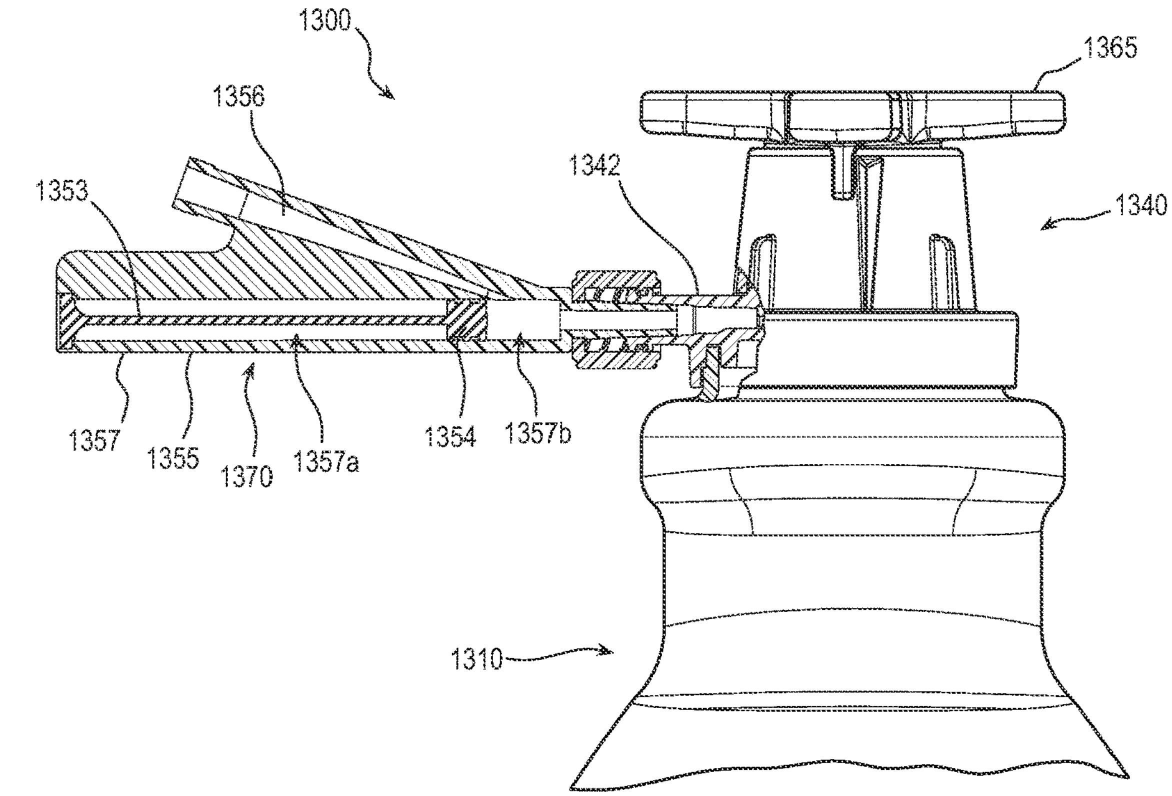
FIG. 15A is a cross-sectional view of an in-line gauge vacuum indicator of another embodiment of a vacuum drainage collection bottle where the in-line gauge is in an activated state.
Figure 15B:
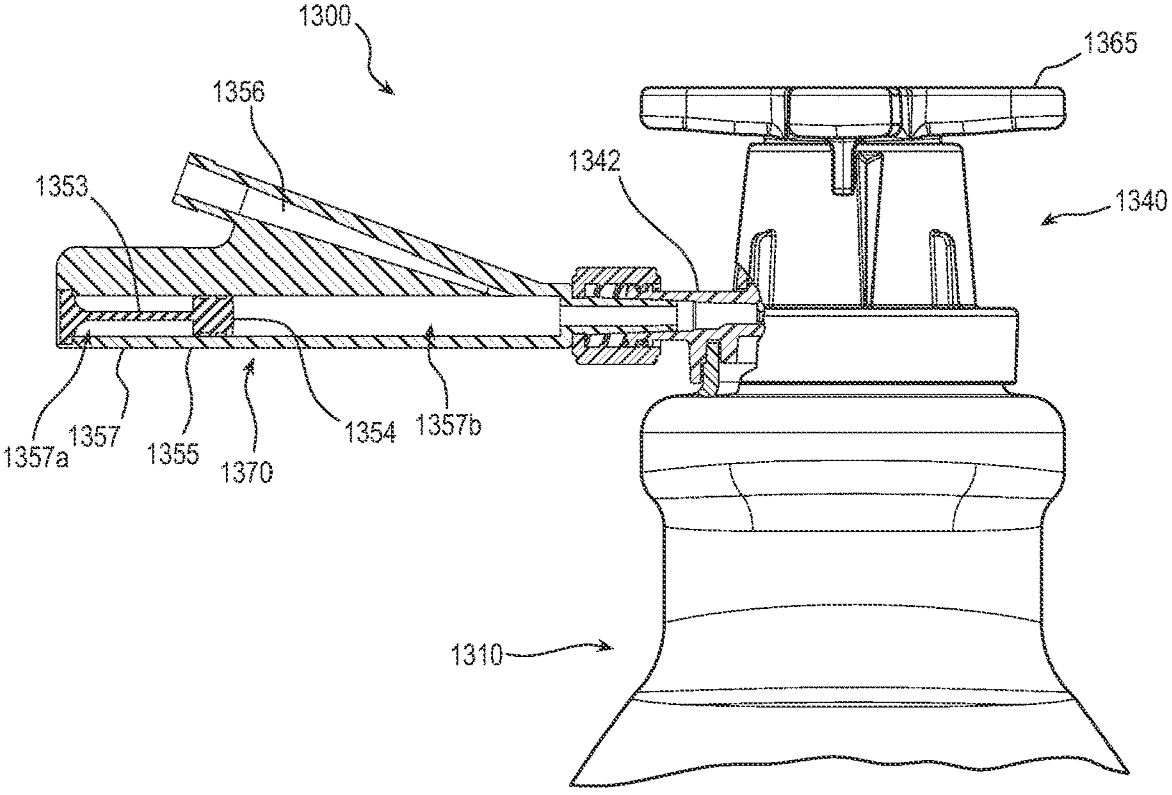
FIG. 15B is a cross-sectional view of the in-line gauge vacuum indicator of the vacuum drainage collection bottle of FIG. 15A where the in-line gauge is in a non-activated state.
Figure 16A:
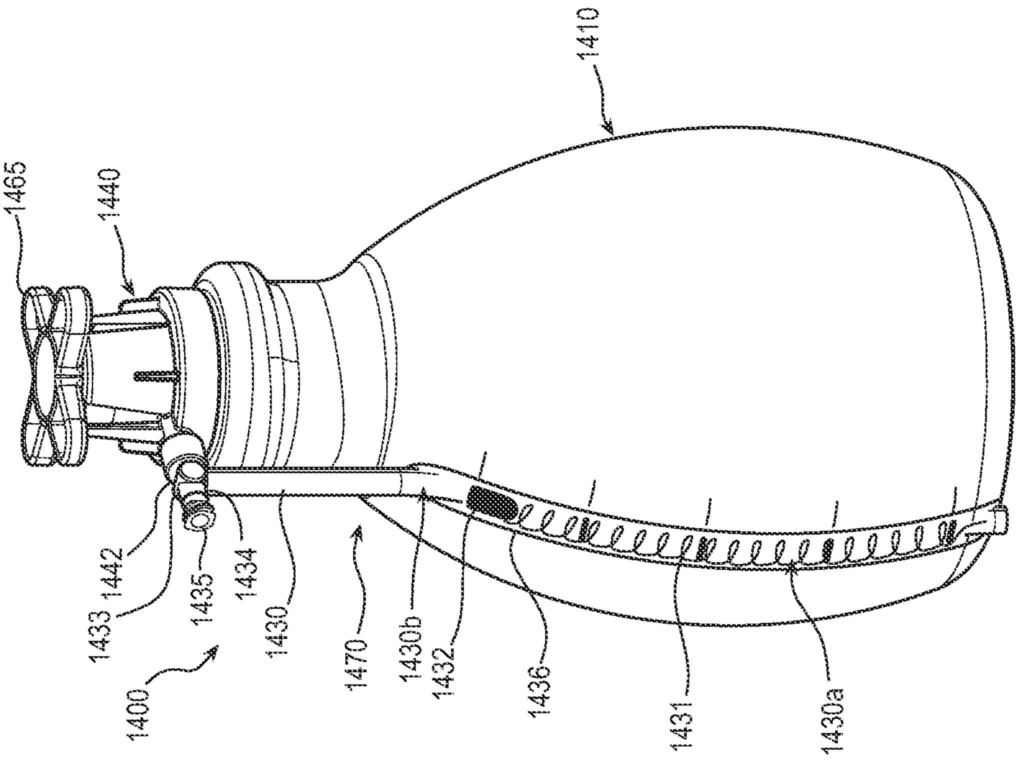
FIG. 16A is a perspective view of another embodiment of a vacuum drainage collection bottle with an integrated tubing vacuum indicator in an activated state.
Figure 16B:
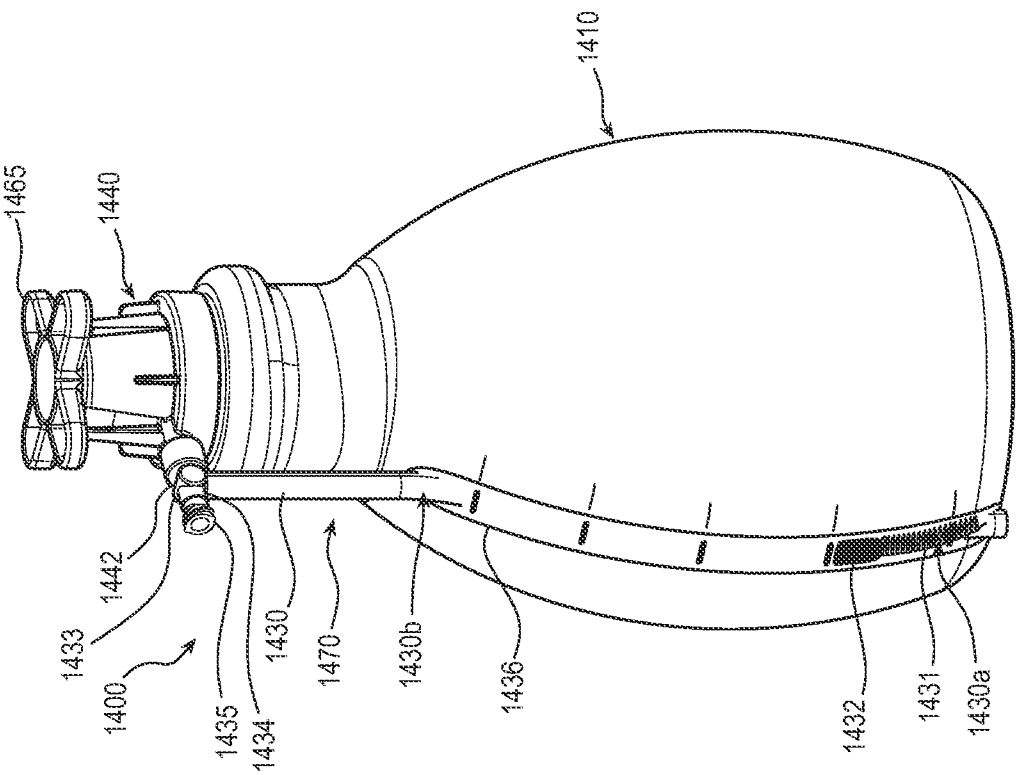
FIG. 16B is a perspective view of the vacuum drainage collection bottle of FIG. 16A with an integrated tubing vacuum indicator in a non-activated state.
Figure 17A:
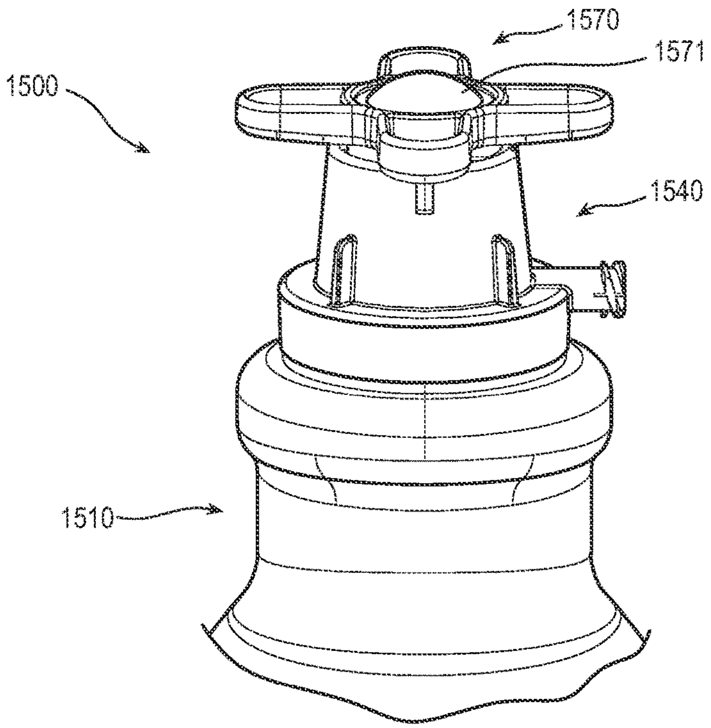
FIG. 17A is a perspective view of a portion of another embodiment of a vacuum drainage collection bottle including a deflectable membrane vacuum indicator.
Figure 17B:
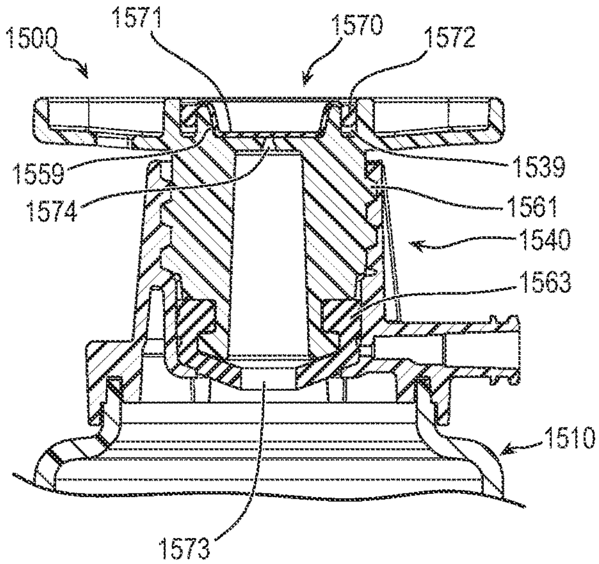
FIG. 17B is a longitudinal cross-sectional view of the portion of the vacuum drainage collection bottle of FIG. 17A with the vacuum indicator in an activated state.
Figure 17C:
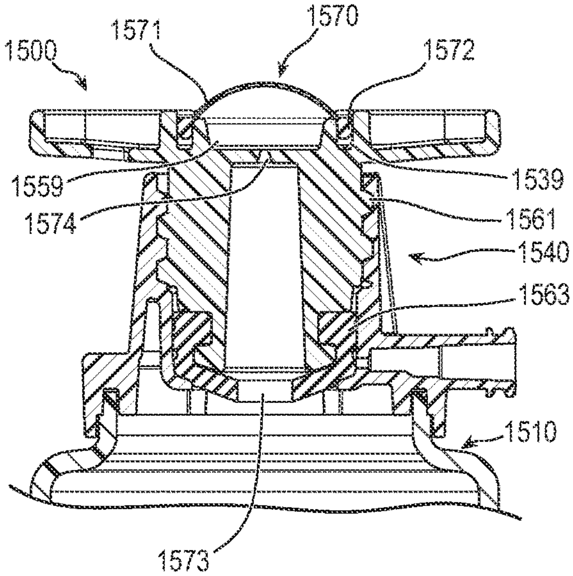
FIG. 17C is a longitudinal cross-sectional view of the portion of the vacuum drainage collection bottle of FIG. 17A with the vacuum indicator in a non-activated state.

FIGS. 1 and 2 illustrate an embodiment of a vacuum drainage collection bottle. FIGS. 3A-3C illustrate an embodiment of a cap of the vacuum drainage collection bottle. FIGS. 4A-4C illustrate another embodiment of a vacuum drainage collection bottle including an elastic membrane vacuum indicator. FIGS. 5A and 5B illustrate another embodiment of a vacuum drainage collection bottle including an expandable vacuum indicator. FIGS. 6A and 6B illustrate another embodiment of a vacuum drainage collection bottle including an expandable member vacuum indicator. FIGS. 7A and 7B illustrate another embodiment of a vacuum drainage collection bottle including an expandable vacuum indicator. FIGS. 8A and 8B illustrate another embodiment of a vacuum drainage collection bottle including an expandable vacuum indicator. FIGS. 9A and 9B illustrate another embodiment of a vacuum drainage collection bottle including a linear vacuum indicator. FIGS. 10A and 10B illustrate another embodiment of a vacuum drainage collection bottle including a digital pressure sensor vacuum indicator. FIGS. 11A-11C illustrate another embodiment of a vacuum drainage collection bottle including an expandable vacuum indicator. FIGS. 12A and 12B illustrate another embodiment of a vacuum drainage collection bottle including an expandable vacuum indicator. FIGS. 13A and 13B illustrate another embodiment of a vacuum drainage collection bottle including a retractable adapter vacuum indicator. FIG. 14 illustrates another embodiment of a vacuum drainage collection bottle including a vacuum gauge vacuum indicator. FIGS. 15A and 15B illustrate another embodiment of a vacuum drainage collection bottle including an in-line vacuum indicator. FIGS. 16A and 16B illustrate another embodiment of a vacuum drainage collection bottle including an integrated tubing vacuum indicator. FIGS. 17A-17C illustrate another embodiment of a vacuum drainage collection bottle including a deflectable membrane vacuum indicator. FIGS. 18A-19B illustrate embodiments of a vacuum drainage collection bottle including an deflectable member vacuum indicator.

In the illustrated embodiment of FIGS. 1 and 2, the vacuum drainage collection bottle 100 includes two broad groups of components; each group may have numerous subcomponents and parts. The two broad component groups are: a receptacle or container 110 and a cap 140. FIG. 2 is an exploded perspective view of the drainage collection bottle embodiment 100. As illustrated in FIG. 2, the container 110 may include a body (or drainage containment) portion 111 and a neck portion 112. The body portion 111 may be a hollow object, which in some embodiments is formed from a transparent, translucent, or opaque, rigid or semi-rigid material, such as glass, plastic, polymeric materials, polycarbonate, polyesters, cyclic olefin copolymers, etc., using any suitable manufacturing technique, such as molding, blow molding, glass blowing, etc. In the illustrated embodiment of FIG. 2, the body portion 111 may have a truncated prolate spheroid shape or truncated football shape with a broad base 122.

As illustrated in FIG. 2, the neck portion 112 may include a rim 117 and a mouth 116. The rim 117 may be circular and can be used to facilitate coupling of the cap 140 to the container 110. The mouth 116 can be an opening defined by the rim 117 and may be configured to allow drainage fluid to flow into and out of the container 110.

In the embodiment of the vacuum drainage collection bottle 100 illustrated in FIG. 2, the cap 140 can include a body 141 and a sealing member 160. In the illustrated embodiment, the body 141 can include an inlet 142, internal threads 145, and a stopper seal surface 148 (shown in FIG. 3A). The body 141 can be sealingly coupled to the container 110 using any suitable technique. For example, as shown in FIG. 3A, the body 141 may include an annular channel 149 configured to receive the rim 117. The annular channel 149 and the rim 117 may be joined together using heat welding, vibration welding, bonding, gluing, spin welding, etc. In other embodiments, the body 141 and the container 110 can be coupled by a snap fit, a frictional fit, a threaded coupling, etc. One or more sealing members can also be used.

The inlet 142, as depicted in FIG. 2, may include an external connector 144 and a fluid channel 143 (shown in FIG. 3A). The external connector 144 can be of any suitable configuration capable of attachment to a drainage tube. For example, as depicted in FIG. 2, the external connector 144 may be a female Luer lock connector configured to receive a male Luer lock connector. In other embodiments, the external connector 144 may be a barbed connector configured to receive a drainage tube without a connector. The fluid channel 143 may pass through a wall of the body 141 and provide fluid communication between the external connector 144 and the container 110 as shown in FIG. 3A. Other types of external connectors 144 can also be used.

As shown in FIG. 2, the internal threads 145 can be configured to threadingly engage with external threads 162 of the sealing member 160 and the stopper seal surface 148 may be configured to sealingly and slidably couple with a stopper 163 of the sealing member 160, as shown in FIG. 3A.

In the illustrated embodiment of FIG. 2, the sealing member 160 may include a plunger 161, the stopper 163 coupled to an end of the plunger 161, and the handle 165 disposed at the end of the plunger 161 opposite the stopper 163. The plunger 161 may include external threads 162 configured to threadingly engage with the internal threads 145 of the body 141.

As depicted in FIG. 2, the stopper 163 may be formed of a compliant material, such as rubber, thermoplastic elastomer, etc. and configured to selectively seal the inlet 142 to prevent passage of drainage fluid through the inlet 142. The stopper 163 may also form a circumferential seal with the stopper seal surface 148 to prevent passage of gas by the stopper 163 to maintain a vacuum within the container 110. In some embodiments, the stopper 163 can include seal rings 164 to provide the circumferential seal with the stopper seal surface 148.

The handle 165 may be configured to rotate the plunger 161 to displace the stopper 163 relative to the fluid channel 143. As depicted in FIG. 2, the handle 165 can include one or more arms 166 (e.g., four arms 166 as illustrated) extending radial outwardly from a central axis of the plunger 161 and spaced circumferentially equidistance. In other embodiments, the number of arms 166 may be 1, 2, 3, 5, or more. In certain embodiments, the handle 165 can include an indicium 169, such as an arrow, to indicate whether the cap 140 is in a closed state or an open state.

FIG. 3A depicts the cap 140 of the vacuum drainage collection bottle 100 in the closed state. In the closed state, as shown in FIG. 3A, the stopper 163 may be disposed against a seal ring 146 of the body 141 such that the stopper 163 can seal the fluid channel 143 of the inlet 142. When sealed, drainage fluid can be prevented from passing through the fluid channel 143 and into the container 110. The stopper 163 can also circumferentially seal against the stopper seal surface 148 to prevent gas from passing by the stopper 163 and reducing the vacuum within the container 110. In the closed state, a rotation stop protrusion 167 may extend downward from the handle 165 and may be positioned about 180 degrees from a rotation stop rib 168 extending radial outwardly from the body 141.

FIG. 3B depicts the cap 140 of the vacuum drainage collection bottle 100 in an open state. The cap 140 can be transitioned to the open state when the handle 165 is rotated in a first direction causing the plunger 161 to rotate. In the open state the stopper 163 may be displaced relative to the fluid channel 143 such that the stopper 163 does not seal the fluid channel 143. When the plunger 161 is rotated, the internal and external threads 145, 162 may engage to displace the plunger 161 and the stopper 163 upward relative to the fluid channel 143. In some embodiments, the handle 165 may be rotated from about one degree to about 180 degrees or more to displace the stopper 163. When the handle 165 is rotated about 180 degrees, the stopper 163 may be displaced upwardly such that the fluid channel 143 is not sealed by the stopper 163 and drainage fluid is allowed to flow freely through the fluid channel 143, which may be caused in part by the vacuum or negative gauge pressure within the vacuum drainage collection bottle 100. When the handle 165 is rotated less than about 180 degrees, the stopper 163 may partially block or seal the fluid channel 143 and drainage fluid flow through the fluid channel 143 may be reduced. It may be advantageous to a patient to selectively reduce the flow of drainage fluid when s/he feels discomfort when the drainage fluid is flowing at a high rate. Further, while rotation of about 180 degrees to open the fluid channel 143 is discussed above, it will be appreciated that the degree of rotation to open and/or close fluid channel 143 can be modified as desired.

In the depicted embodiment of the cap 140 of FIG. 3B, when the handle 165 is rotated about 180 degrees from the closed state, the rotation stop protrusion 167 may be engaged with a rotation stop rib 168. The rotation stop protrusion 167 can engage with the rotation stop rib 168 to provide a tactile feedback to the user that the cap 140 is in a fully open state. In some embodiments, the rotation stop protrusion 167 and the rotation stop rib 168 may be of any suitable configuration. For example, the rotation stop protrusion 167 can be a deflectable lever that is captured between two rotation stop ribs 168 to prevent the handle 165 from further rotation. In this embodiment, the rotation stop protrusion 167 may be deflected by the user to allow the handle 165 to be rotated in either direction.

Further rotation of the handle 165 may cause the rotation stop protrusion 167 to be deflected by the rotation stop rib 168 and allow the sealing member 160 to be removed from the cap 140 as shown in FIG. 3C. In some embodiments, when the sealing member 160 is removed from the cap 140, drainage fluid within the container 110 can be poured out through the body 141 of the cap 140.

FIGS. 4A-4C illustrate another embodiment of a vacuum drainage collection bottle 200. In the illustrated embodiment of FIG. 4A, the vacuum drainage collection bottle 200 includes a container 210 and a cap 240 coupled to the container 210. A vacuum indicator 270 configured to indicate a vacuum or negative gauge pressure within the container 210 is coupled to the cap 240. The vacuum indicator 270 includes an elastic membrane 271 and a retention member 272 configured to couple the elastic membrane 271 to the cap 240. The elastic membrane 271 can be formed of any suitable elastomeric material to allow the elastic membrane 271 to be deformed and/or stretched and then substantially return to an original state. For example, the elastic membrane 271 can include latex, a thermoplastic elastomer, silicone, rubber, and/or natural and synthetic rubbers/elastomers, such as polyvinyl chloride, styrene, nitrile, polymer polychloroprene and polyurethane. Other elastomeric materials are contemplated. In certain embodiments the elastic member 271 may include a barrier coating.

FIG. 4B illustrates the vacuum indicator 270 in an activated state where the elastic membrane 271 is deformed or in a stretched state due to a vacuum or negative gauge pressure within the container 210. As illustrated, the elastic membrane 271 is coupled to the retention member 272, which is coupled to a plunger 261 of the cap 240. The retention member 272 includes a bore 287 that is in communication with a plunger bore 259. The plunger bore 259 is in communication with the container 210 via a plunger channel 274 through a distal wall of the plunger 261 and via a stopper channel 273 through a distal wall of a stopper 263. When the elastic membrane 271 is exposed to the vacuum or negative gauge pressure of the container 210, the elastic membrane 271 is deformed and/or stretched into the plunger bore 259 by the pressure differential caused by the vacuum or negative gauge pressure in the container 210.

FIG. 4C illustrates vacuum indicator 270 in a non-activated state where the elastic membrane 271 is relaxed or in a contracted state due to depletion of the vacuum within the container 210. In other words, the pressure within the container 210 is equal to or substantially equal to the atmospheric or ambient pressure outside the container 210. As illustrated, the elastic membrane 271 extends over the plunger bore 259 but is not deformed or stretched into the plunger bore 259. The non-activated state is further due to the elasticity of the elastic membrane 271.

The deformation and contraction of the elastic membrane 271 may allow a user to determine a relative level of the vacuum or negative gauge pressure within the container 210. For example, when the elastic membrane 271 is relaxed (e.g., not deformed or stretched), the user may determine that the vacuum or negative gauge pressure within the container 210 is depleted or nearly depleted. In other words, the pressure within the container 210 is substantially equal to the atmospheric or ambient pressure outside the container 210. In this state, the user may not be able to either start or finish a drainage procedure. Further, when the elastic membrane 271 is deformed and/or stretched, the user may determine that there is adequate vacuum or negative gauge pressure within the container 210 to either start or continue a drainage procedure. In certain embodiments, the vacuum of the container 210 may be reduced over time as the vacuum drainage collection bottle 200 sits on a storage shelf ready for use. The vacuum can also be depleted as air leaks into the container 210 through seams, junctions, and walls of the vacuum collection drainage bottle 200. In other embodiments, the vacuum of the container 210 can be depleted during the drainage procedure as drainage fluid is drawn from the patient and replaces the vacuum of the container 210.

FIGS. 5A and 5B illustrate another embodiment of a vacuum drainage collection bottle 300. In the illustrated embodiment of FIG. 5A, the vacuum drainage collection bottle 300 includes a container 310 and a cap 340 coupled to the container 310. A vacuum indicator 370 configured to indicate a vacuum or negative gauge pressure within the container 310 is coupled to the cap 340. The vacuum indicator 370 includes an expandable member 375 (e.g., a balloon) coupled to a stopper 363 and a plunger 361. In some embodiments, an end of the expandable member 375 may extend through a stopper channel 373 of the stopper 363 and be disposed between the plunger 361 and the stopper 363. The expandable member 375 can be formed of any suitable elastomeric material to allow the expandable member 375 to be expanded and then substantially return to an original state. For example, the expandable member 375 can include latex, thermoplastic elastomer, polyethylene terephthalate (PET), nylon, rubber, and/or natural and synthetic rubbers/elastomers, such as polyvinyl chloride, styrene, nitrile, polymer polychloroprene and polyurethane. Other elastomeric materials are contemplated. In certain embodiments the expandable member 375 may include a barrier coating.

FIG. 5A depicts the vacuum indicator 370 in an activated state where the expandable member 375 is expanded. When the expandable member 375 is exposed to a vacuum or negative gauge pressure of the container 310, the expandable member 375 is expanded into the container 310 due to the pressure differential between the inside of the expandable member 375 and the inside of the container 310. For instance, the inside of the expandable member 375 may be at approximately atmospheric or ambient pressure. When the pressure inside of the container 310 is less than atmospheric or ambient pressure (e.g., a vacuum or negative gauge pressure), the expandable member 375 may expand and increase in size as shown in FIG. 5A.

FIG. 5B illustrates the vacuum indicator 370 in a non-activated state where the expandable member 375 is relaxed or contracted due to depletion of the vacuum within the container 310. In other words, the pressure inside the expandable member 375 is now approximately equal to the pressure inside the container 310. As illustrated, a diameter of the expandable member 375 of FIG. 5B is smaller than a diameter of the expandable member 375 of 5A when the vacuum indicator 370 is in the activated state.

The expansion and contraction of the expandable member 375 may allow a user to determine a relative level of vacuum or negative gauge pressure within the container 310. For example, when the expandable member 375 is relaxed or contracted, the user may determine that the vacuum or negative gauge pressure of the container 310 is depleted or nearly depleted. In other words, the pressure within the container 310 is substantially equal to the atmospheric or ambient pressure in the expandable member 375. In this state, the user may not be able to either start or finish a drainage procedure. Further, when the expandable member 375 is expanded, the user may determine that there is adequate vacuum or negative gauge pressure to either start or continue a drainage procedure.

FIGS. 6A and 6B illustrate another embodiment of a vacuum drainage collection bottle 400. In the illustrated embodiment of FIG. 6A, the vacuum drainage collection bottle 400 includes a container 410 and a cap 440 coupled to the container 410. A vacuum indicator 470 configured to indicate a vacuum or negative gauge pressure within the container 410 is coupled to the cap 440. The vacuum indicator 470 includes an expandable member 475 (e.g., a straw or tube) coupled to a stopper 463 and a plunger 361. The expandable member 475 can be preformed to have a non-straight shape, such as a spiral, curled, or bent shape. Other non-straight shapes are contemplated. At least one end of the expandable member 475 is closed. In some embodiments, an end of the expandable member 475 may extend through a stopper channel 473 of the stopper 463 and be disposed between the plunger 461 and the stopper 463. The expandable member 475 can be formed of any suitable flexible material to allow the expandable member 475 to be straightened and then substantially returned to a preformed non-straight state. For example, the expandable member 475 can include polyethylene, polypropylene, thermoplastic elastomer, polyethylene terephthalate (PET), nylon, silicone, rubber, and/or natural and synthetic rubbers/elastomers, such as Mylar, polyvinyl chloride, styrene, nitrile, polymer polychloroprene and polyurethane. Other flexible materials are contemplated. In certain embodiments the expandable member 475 may include a barrier coating.

FIG. 6A depicts the vacuum indicator 470 in an activated state where the expandable member 475 is substantially straight. When the expandable member 475 is exposed to a vacuum or negative gauge pressure of the container 410, the expandable member 475 is straightened into the container 410 due to the pressure differential between the inside of the expandable member 475 and the inside of the container 410. For instance, the inside of the expandable member 475 may be at approximately atmospheric or ambient pressure. When the pressure inside of the container 410 is less than atmospheric or ambient pressure (e.g., a vacuum or negative gauge pressure), the expandable member 375 may straighten and/or expand as shown in FIG. 6A.

FIG. 6B illustrates the vacuum indicator 470 in a non-activated state where the expandable member 475 is spiraled, bent, or curled due to depletion of the vacuum within the container 410. In other words, the pressure inside the expandable member 475 is now approximately equal to the pressure inside the container 410. As illustrated, the straightness of the expandable member 475 of FIG. 6B is less than the straightness of the expandable member 475 of FIG. 6A when the vacuum indicator 470 is in the activated state.

The expansion and contraction of the expandable member 475 may allow a user to determine a relative level of vacuum or negative gauge pressure within the container 410. For example, when the expandable member 475 is spiraled, bent, or curled, the user may determine that the vacuum or negative gauge pressure of the container 410 is depleted or nearly depleted. In other words, the pressure within the container 410 is substantially equal to the atmospheric or ambient pressure in the expandable member 475. In this state, the user may not be able to either start or finish a drainage procedure. Further, when the expandable member 475 is substantially straight, the user may determine that there is adequate vacuum or negative gauge pressure to either start or continue a drainage procedure.

FIGS. 7A and 7B illustrate another embodiment of a vacuum drainage collection bottle 500. In the illustrated embodiment of FIG. 7A, the vacuum drainage collection bottle 500 includes a container 510 and a cap 540 coupled to the container 510. A vacuum indicator 570 configured to indicate a vacuum or negative gauge pressure within the container 510 is disposed within the container 510. The vacuum indicator 570 includes an expandable member 576 (e.g., a hollow sphere or ball) disposed inside the container 510. The expandable member 576 may be filled with air or other suitable inert gas, such as nitrogen, argon, helium, etc., that has a low permeability across a wall of the expandable member 576. A wall of the expandable member 576 can be formed of any suitable elastomeric material to allow the expandable member 576 to be expanded and then substantially contracted to an original size. For example, the expandable member 576 can include latex, thermoplastic elastomer, polyethylene terephthalate (PET), nylon, rubber, and/or natural and synthetic rubbers/elastomers, such as polyvinyl chloride, styrene, nitrile, polymer polychloroprene and polyurethane. Other elastomeric materials are contemplated. In certain embodiments the expandable member 576 may include a barrier coating.

FIG. 7A illustrates the vacuum indicator 570 in an activated state where the expandable member 576 is expanded. When the expandable member 576 is exposed to a vacuum or negative gauge pressure of the container 510, the expandable member 576 is expanded to fill a portion of the container 510 due to the pressure differential between the inside of the expandable member 576 and the inside of the container 510. For instance, the inside of the expandable member 576 may be at approximately atmospheric or ambient pressure. When the pressure inside of the container 510 is less than atmospheric or ambient pressure (e.g., a vacuum or negative gauge pressure), the expandable member 576 may expand and increase in size as shown in FIG. 7A.

FIG. 7B depicts the vacuum indicator 570 in a non-activated state where the expandable member 576 is relaxed or contracted due to depletion of the vacuum within the container 510. In other words, the pressure inside the expandable member 576 is now approximately equal to the pressure inside the container 510. As depicted, a diameter of the expandable member 576 of FIG. 7B is smaller than the diameter of the expandable 576 of FIG. 7A when the expandable member 576 is expanded.

Expansion and contraction of the expandable member 576 may allow a user to determine a relative level of the vacuum or negative gauge pressure within the container 510. For example, when the expandable member 576 is relaxed, the user may determine that the vacuum or negative gauge pressure of the container 510 is depleted or near depletion. In other words, the pressure within the container 510 is substantially equal to the atmospheric or ambient pressure in the expandable member 576. In this state, the user may not be able to either start or finish a drainage procedure. Further, when the expandable member 576 is expanded, the user may determine that there is adequate vacuum or negative gauge pressure to either start or continue a drainage procedure.

FIGS. 8A and 8B illustrate another embodiment of a vacuum drainage collection bottle 600. In the illustrated embodiment of FIG. 8A, the vacuum drainage collection bottle 600 includes a container 610 and a cap 640 coupled to the container 610. A vacuum indicator 670 configured to indicate a vacuum or negative gauge pressure within the container 610 is disposed within the container 610. The vacuum indicator 670 includes an expandable member 676 (e.g., a straw or tube) disposed inside the container 610. The expandable member 676 can be preformed to have a non-straight shape, such as a spiral, curled, or bent shape. Other non-straight shapes are contemplated. The ends of the expandable member 676 are closed. The expandable member 676 may be filled with air or other suitable inert gas, such as nitrogen, argon, helium, etc., that has a low permeability across a wall of the expandable member 576. A wall of the expandable member 676 can be formed of any suitable flexible material to allow the expandable member 676 to be substantially straightened and then returned to a preformed non-straight state. For example, the expandable member 676 can include polyethylene, polypropylene, thermoplastic elastomer, polyethylene terephthalate (PET), nylon, rubber, and/or natural and synthetic rubbers/elastomers, such as polyvinyl chloride, styrene, nitrile, polymer polychloroprene and polyurethane. Other flexible materials are contemplated. In certain embodiments the expandable member 676 may include a barrier coating FIG. 8A illustrates the vacuum indicator 670 in an activated state where the expandable member 676 is straightened and/or expanded. When the expandable member 676 is exposed to a vacuum or negative gauge pressure of the container 610, the expandable member 676 is straightened due to the pressure differential between the inside of the expandable member 676 and the inside of the container 610. For instance, the inside of the expandable member 676 may be at approximately atmospheric or ambient pressure. When the pressure inside of the container 610 is less than atmospheric or ambient pressure (e.g., a vacuum or negative gauge pressure), the expandable member 676 may straighten or expand as shown in FIG. 8A.

FIG. 8B depicts the vacuum indicator 670 in a non-activated state where the expandable member 676 is spiraled, bent, or curled due to depletion of the vacuum within the container 610. In other words, the pressure inside the expandable member 676 is now approximately equal to the pressure inside the container 610. As depicted, a straightness of the expandable member 676 of FIG. 8B is less than the straightness of the expandable member 676 of FIG. 8A when the expandable member 676 is in the activated state.

Expansion and contraction of the expandable member 676 may allow a user to determine a relative level of the vacuum or negative gauge pressure within the container 610. For example, when the expandable member 676 is spiraled, bent, or curled, the user may determine that the vacuum or negative gauge pressure of the container 610 is depleted or near depletion. In other words, the pressure within the container 610 is substantially equal to the atmospheric or ambient pressure in the expandable member 676. In this state, the user may not be able to either start or finish a drainage procedure. Further, when the expandable member 676 is substantially straight, the user may determine that there is adequate vacuum or negative gauge pressure to either start or continue a drainage procedure.

FIGS. 9A and 9B illustrate another embodiment of a vacuum drainage collection bottle 700. In the illustrated embodiment of FIG. 9A, the vacuum drainage collection bottle 700 includes a container 710 and a cap 740 coupled to the container 710. A vacuum indicator 770 configured to indicate a vacuum or negative gauge pressure within the container 710 is coupled to the cap 740. The vacuum indicator 770 includes a linear vacuum gauge 789. The linear vacuum gauge 789 includes a tubular body 777, an indicator plunger 779, and a seal member 780.

As illustrated in FIG. 9A, in some embodiments the tubular body 777 is coupled to a plunger 761 of the cap 740. The tubular body 777 further extends through or is coupled to the stopper 763 of the cap 740. The tubular body 777 includes a retention ring 778 disposed adjacent an open distal end of a bore 790. A diameter of the bore 790 is sized to slidingly receive the indicator plunger 779 and the seal member 780. The indicator plunger 779 includes a retention flange 781 disposed adjacent a proximal end. A diameter of the retention flange 781 is larger than a diameter of the bore 790 at the retention ring 778 such that the indicator plunger 779 can be retained within the tubular body 777. The indicator plunger 779 may further include an indicium. In some embodiments, the indicium is a color, such as green. In other embodiments, a proximal portion of the indicator plunger 779 may be green and a distal portion may be red. In another embodiment, the indicium can include a number scale. The seal member 780 is shown coupled to the proximal end of the indicator plunger 779. The seal member 780 can be formed of an elastomeric material such that the seal member 780 can sealingly engage an internal surface of the tubular body 777. For example, the seal member 780 may be formed of natural rubber, latex, silicone, or thermoplastic elastomer. Other elastomeric materials are contemplated.

FIG. 9A illustrates the vacuum indicator 770 in an activated state. In the activated state, the indicator plunger 779 extends beyond the tubular body 777 into the container 710 due to the pressure differential between the inside of the tubular body 777 and the inside of the container 710. When extended the indicator plunger 779 is visible to the user. When the indicator plunger 779 is extended, a vacuum or negative gauge pressure is generated in a proximal portion of the tubular body 777. The indicator plunger 779 can be extended until the vacuum or negative gauge pressure in the container 710 is substantially equivalent to the vacuum or negative gauge pressure in the tubular body 777.

FIG. 9B illustrates the vacuum indicator 770 in a non-activated state. In the non-activated state, the indicator plunger 779 is retracted into the tubular body 777 such that the indicator plunger 779 is not visible to the user. The vacuum or negative gauge pressure created within the tubular body 777 can cause retraction of the indicator plunger 779 as the vacuum within the container 710 is reduced towards atmospheric or ambient pressure.

The extension and retraction of the indicator plunger 779 may allow a user to determine a relative level of the vacuum within the container 710. For example, when the indicator plunger 779 is retracted and not visible to the user, the user may determine that the vacuum or negative gauge pressure of the container 710 is depleted or nearly depleted. The user may not be able to either start or finish a drainage procedure. Further, when the indicator plunger 779 is extended and visible to the user, the user may determine that there is adequate vacuum or negative gauge pressure within the container 710 to either start or continue a drainage procedure. In some embodiments, the indicator plunger 779 may be partially retracted into the tubular body 777 with a distal portion of the indicator plunger 779 extending beyond the tubular body 777. In this embodiment, the distal portion may include an indicium to indicate to the user a depletion of the vacuum. For example, the distal extending portion may be colored red while the remainder of the indicator plunger 779 may be colored green. When only the red portion of the indicator plunger 779 is visible, the user can determine that the vacuum or negative gauge pressure of the container 710 is inadequate to start or complete a drainage procedure.

FIGS. 10A and 10B illustrate another embodiment of a vacuum drainage collection bottle 800. In the illustrated embodiment of FIG. 10A, the vacuum drainage collection bottle 800 includes a container 810 and a cap 840 coupled to the container 810. A vacuum indicator 870 configured to indicate a vacuum or negative gauge pressure within the container 810 is coupled to the cap 840. The vacuum indicator 870 includes an electrical pressure gauge 893.

In the illustrated embodiment of FIG. 10B, the electrical pressure gauge 893 can include a housing 894, a pressure sensor 883, a circuit board 884, a switch 885, a power source 886, and an indicium 882. The housing 894 is disposed within a handle 865 of the cap 840 and defines a chamber 895. The pressure sensor 883 is disposed within the chamber 895 and is in communication with a vacuum or negative gauge pressure within the container 810 through a channel 873 of a stopper 863. The pressure sensor 883 may be of any suitable type to measure a pressure or vacuum and transmit a digital and/or analog signal to the circuit board 884. The power source 886 can be disposed within the chamber 895 and may comprise one or more batteries.

The switch 885 is disposed at a proximal end of the housing 894 and is positioned such that it can be actuated by a user. In one embodiment, the switch 885 can be a momentary switch that is actuated when depressed with digital pressure (e.g., the push of a finger) and is deactuated when the digital pressure is released and the momentary switch returns to a substantially neutral position. Other types of switches, such as rocker, push button, toggle, etc., are also contemplated within the scope of this disclosure. When actuated, the switch 885 can cause the indicium 882 to be activated. As shown in the illustrated embodiment, the indicium 882 is disposed at the proximal end of the housing 894 adjacent the switch 885 and positioned such that a user can visualize the indicium 882. In the illustrated embodiment, the indicium 882 includes two light emitting diodes (LEDs). Each of the LEDs can emit a different color of visible light. For example, one LED may emit a red visible light and the other LED may emit a green visible light. In other embodiments, the indicium 882 may include a single LED configured to emit two different visible colors, such as red and green. In another embodiment, the indicium 882 may include three or more LEDs configured to indicate a different level of vacuum. For example, the indicium 882 can include five LEDs. When all five LEDs are activated, a vacuum level of 100% is indicated, when four LEDs are activated, a vacuum level of 80% is indicated, when, three of the LEDs are activated, a vacuum level of 60% is indicated, and etc. Other numbers and/or LEDs arrangements can also be used in similar fashion. Other types of indicia 882 are also contemplated.

In the illustrated embodiment, the circuit board 884 is disposed within the chamber 895 and electrically coupled to the pressure sensor 883, the switch 885, and the indicium 882. The circuit board 884 can be a printed circuit board. Optionally, the circuit board 884, the switch 885, the power source 886, and the indicium 882 or a display may be disposed within a handheld device that is coupled to the pressure sensor 883 via a wire and a connector. The circuit board 884 may include a threshold pressure value stored in a memory member. The threshold pressure value may be used to activate a change to the indicium 882. For example, when the pressure sensor 883 detects a pressure (e.g., negative gauge pressure) within the container 810 that is less than the threshold pressure value, the circuit board 884 can activate the indicium 882 (e.g., green LED) when the switch 885 is actuated to indicate to a user that the vacuum or negative gauge pressure of the container 810 may be adequate to start or continue with a drainage procedure. Further, when the pressure sensor 883 detects a pressure (e.g., negative gauge pressure) within the container 810 that is greater than the threshold pressure value, the circuit board 884 can activate the indicium 882 (e.g., red LED) when the switch 885 is actuated to indicate to the user that there may be inadequate vacuum or negative gauge pressure within the container 810 to start or complete a drainage procedure. In another embodiment, the circuit board 884 may perform the logic of activating a different number of LEDs based on a level of pressure that is detected within the container 810.

FIGS. 11A-11C illustrate another embodiment of a vacuum drainage collection bottle 900. In the illustrated embodiment of FIG. 11A, the vacuum drainage collection bottle 900 includes a container 910 and a cap 940 coupled to the container 910. A vacuum indicator 970 configured to indicate a vacuum or negative gauge pressure within the container 910 is disposed within the container 910. The vacuum indicator 970 includes an expandable member 996. In some embodiments, the expandable member 996 comprises a sealed bag.

FIG. 11B illustrates the expandable member 996 prior to sealing. The bag 996 may be formed from a sheet 999 of flexible material, such as polyethylene or polypropylene. Other materials are contemplated. In the illustrated embodiment, the sheet 999 includes a translucent portion 997. In other embodiments, the sheet 999 may be fully translucent. An indicium 998 is disposed on an inner surface of the expandable member 996. In certain embodiments, the indicium 998 can be printed directly on the sheet 999. In some embodiments, the indicium 998 may be a label coupled to the inner surface. The indicium 998 can include printed words, phrases, or symbols to indicate a depletion of a vacuum within the container 910. For example, as illustrated in FIG. 11B, the indicium 998 includes the phrase "No Vacuum." Other words, phrases, and symbols are contemplated. During assembly, the sheet 999 can be folded in half such that the translucent portion 997 overlays the indicium 998. Further, free edges of the sheet 999 can be sealed together to form the expandable member 996 with a small amount of air inside.

FIG. 11A depicts the vacuum indicator 970 in an activated state where the expandable member 996 is expanded within the container 910 due to the pressure differential between the inside of the expandable member 996 and the inside of the container 910. For instance, the inside of the expandable member 996 may be at approximately atmospheric or ambient pressure. When the pressure inside of the container 910 is less than atmospheric or ambient pressure (e.g., a vacuum or negative gauge pressure), the bag expandable member may expand and increase in size as shown in FIG. 11A. When expanded, the translucent portion 997 can pull away from the indicium 998 such that the indicium 998 may not be visible to a user through the translucent portion 997.

FIG. 11C illustrates the vacuum indicator 970 in a non-activated state where the expandable member 996 is relaxed or contracted due to depletion of the vacuum within the container 910. In other words, the pressure inside the expandable member 996 is now approximately equal to the pressure inside the container 910. As illustrated, a volume of the expandable member 996 of FIG. 11C is smaller than a volume of the expandable member 996 of FIG. 11A. When relaxed, the translucent portion 997 can contact or overlay the indicium 998 such that the indicium 998 is visible through the translucent portion 997 as illustrated in FIG. 11C.

The expansion and contraction of the expandable member 996 may allow a user to determine a relative level of the vacuum or negative gauge pressure within the container 910. For example, when the expandable member 996 is in the relaxed state and the indicium 998 is visible to the user, the user may determine that the vacuum or negative gauge pressure of the container 910 is depleted or nearly depleted. In other words, the pressure within the container 910 is substantially equal to the atmospheric or ambient pressure in the expandable member 996. In this state, the user may not be able to either start or finish a drainage procedure. Further, when the expandable member 996 is expanded and the indicium 998 is not visible to the user through the translucent portion 997, the user may determine that there is adequate vacuum or negative gauge pressure within the container 910 to either start or continue a drainage procedure.

FIGS. 12A and 12B illustrate another embodiment of a vacuum drainage collection bottle 1000. In the illustrated embodiment of FIG. 12A, the vacuum drainage collection bottle 1000 includes a container 1010 and a cap 1040 coupled to the container 1010. A vacuum indicator 1070 configured to indicate a vacuum or negative gauge pressure within the container 1010 is disposed within the container 1010. The vacuum indicator 1070 includes an expandable member 1096.

The expandable member 1096 may be formed from a sheet or membrane 1099 of flexible material, such as polyethylene or polypropylene. Other materials are contemplated. The sheet 1099 is disposed adjacent a bottom portion of the container 1010 and sealingly coupled to an interior surface of the container. In the illustrated embodiment, the sheet 1099 includes a translucent portion 1097. In other embodiments, the sheet 1099 may be fully translucent. An indicium 1098 is disposed on an inner surface of the container 1010 adjacent the bottom portion. In certain embodiments, the indicium 1098 can be printed directly on the inner surface. In some embodiments, the indicium 1098 may be a label coupled to the inner surface. The indicium 1098 can include printed words, phrases, or symbols to indicate a depletion of a vacuum within the container 1010. For example, as illustrated in FIG. 12B, the indicium 1098 includes the phrase "No Vacuum." Other words, phrases, and symbols are contemplated.

FIG. 12A depicts the vacuum indicator 1070 in an activated state where the expandable member 1096 is expanded within the container 1010 due to the pressure differential between the inside of the expandable member 1096 and the inside of the container 1010. For instance, the inside of the expandable member 1096 may be at approximately atmospheric or ambient pressure. When the pressure inside of the container 1010 is less than atmospheric or ambient pressure (e.g., a vacuum or negative gauge pressure), the expandable member 1096 may expand to form a dome shape as shown in FIG. 12A. When expanded, the translucent portion 1097 can pull away from the indicium 1098 such that the indicium 1098 may not be visible to a user through the translucent portion 1097.

FIG. 12B illustrates the vacuum indicator 1070 in a non-activated state where the expandable member 1096 is relaxed or contracted due to depletion of the vacuum within the container 1010. In other words, the pressure inside the expandable member 1096 is now approximately equal to the pressure inside the container 1010. As illustrated, a volume of the expandable member 1096 of FIG. 12B is smaller than a volume of the expandable member 1096 of FIG. 12A. When relaxed, the translucent portion 1097 can contact or overlay the indicium 1098 such that the indicium 1098 is visible through the translucent portion 1097 as illustrated in FIG. 12B.

The expansion and contraction of the expandable member 1096 may allow a user to determine a relative level of the vacuum or negative gauge pressure within the container 1010. For example, when the expandable member 1096 is in the relaxed state and the indicium 1098 is visible to the user, the user may determine that the vacuum or negative gauge pressure of the container 1010 is depleted or nearly depleted. In other words, the pressure within the container 1010 is substantially equal to the atmospheric or ambient pressure in the expandable member 1096. In this state, the user may not be able to either start or finish a drainage procedure. Further, when the expandable member 1096 is expanded and the indicium 1098 is not visible to the user through the translucent portion 1097, the user may determine that there is adequate vacuum or negative gauge pressure within the container 1010 to either start or continue a drainage procedure.

FIGS. 13A and 13B illustrate another embodiment of a vacuum drainage collection bottle 1100. In the illustrated embodiment of FIG. 13A, the vacuum drainage collection bottle 1100 includes a container 1110 and a cap 1140 coupled to the container 1110. A vacuum indicator 1170 configured to indicate a vacuum or negative gauge pressure within the container 1110 is coupled to the cap 1140. The vacuum indicator 1170 includes an adapter 1150, an O-ring 1151, and a resilient member 1152. The adapter 1150 is slidingly disposed within a plunger bore 1159 of a handle 1165 of the cap 1140. The adapter 1150 may include an indicium 1198 disposed at a top portion. The indicium 1198 can be a color, such as red, to indicate a depletion of the vacuum within the container 1110. Other indicia such as words or symbols are contemplated. The O-ring 1151 is circumferentially disposed around the adapter 1150 to seal the plunger bore 1159. The resilient member 1152 is disposed between the adapter 1150 and a plunger 1161. In some embodiments, the resilient member 1152 comprises a compression spring. Other types of resilient members are also contemplated.

FIG. 13A illustrates the vacuum indicator 1170 in an activated state where the adapter 1150 is in a retracted position within the plunger bore 1159 due to the pressure differential between the inside of the container 1110 and the outside of the container 1110. The adapter 1150 is in communication with the vacuum or negative gauge pressure inside the container 1110 through a stopper channel 1173 of a stopper 1163 and a plunger channel 1174 of the plunger 1161. When the adapter 1150 is exposed to the vacuum or negative gauge pressure of the container 1110, the adapter 1150 can be retracted into the plunger bore 1159 toward the container 1110 and the resilient member 1152 can be compressed.

FIG. 13B illustrates the vacuum indicator 1170 in a non-activated state where the adapter 1150 is in a non-retracted position within the plunger bore 1159 due to depletion of the vacuum within the container 1110. In other words, the pressure inside the container 1110 is now approximately equal to the pressure outside the container 1110. As illustrated, the adapter 1150 is disposed adjacent an opening of the plunger bore 1159 such that the indicium 1198 is visible to a user. The adapter 1150 is disposed in the non-retracted position when the vacuum pressure is depleted or partially depleted and the resilient member 1152 applies a force that is greater than the vacuum to the adapter 1150.

The transition of the adapter 1150 from the retracted position to the non-retracted position may allow the user to determine a relative level of the vacuum or negative gauge pressure within the container 1110. For example, when the adapter 1150 is in the retracted position and the indicium 1198 may not be visible to the user, the user may determine that the vacuum or negative gauge pressure within the container 1110 is adequate to start or continue a drainage procedure. When the adapter 1150 is in the non-retracted position, the indicium 1198 may be visible to the user. The user may determine that the vacuum within the container 1110 is depleted or nearly depleted and is inadequate to start or continue a drainage procedure.

FIG. 14 illustrates another embodiment of a vacuum drainage collection bottle 1200. In the illustrated embodiment of FIG. 14, the vacuum drainage collection bottle 1200 includes a container 1210 and a cap 1240 coupled to the container 1210. A vacuum indicator 1270 configured to indicate a vacuum or negative gauge pressure within the container 1210 is shown coupled to the cap 1240. The vacuum indicator 1270 includes a handle 1265 and vacuum gauge 1258. The handle 1265 can be circular in shape and include any suitable grip enhancing features to facilitate rotation of the handle 1265. For example, the grip enhancing features may include ribs, bumps, dimples, a textured surface, or a compliant material. Other grip enhancing features are also contemplated. The vacuum gauge 1258 is disposed within the handle 1265. In the depicted embodiment, the vacuum gauge 1258 is an analog vacuum gauge including a needle 1257 and indicia 1256. In other embodiments, the vacuum gauge 1258 may be a digital vacuum gauge with a digital display. The vacuum gauge 1258 is in communication with the pressure of the container 1210. When the vacuum gauge 1258 is exposed to a vacuum or negative gauge pressure of the container 1210, the needle 1257 can be rotationally displaced to indicate a level of the vacuum or negative gauge pressure within the container 1210. By observing a position of the needle 1257 relative to the indicia 1256, the user may determine a pressure level within the container 1210 and determine if the vacuum or negative gauge pressure is adequate to start or continue a drainage procedure.

FIGS. 15A and 15B illustrate another embodiment of a vacuum drainage collection bottle 1300. In the illustrated embodiment of FIG. 15A, the vacuum drainage collection bottle 1300 includes a container 1310 and a cap 1340 coupled to the container 1310. A vacuum indicator 1370 configured to indicate a vacuum or negative gauge pressure within the container 1310 is shown coupled to an inlet 1342 of the cap 1240. In certain embodiments, the vacuum indicator 1370 may be provided to a user as a separate component that is later coupled to a cap or a container (similar to or different than the cap 1340 and/or container 1310 disclosed herein) by the user. The vacuum indicator 1370 includes an adapter 1355. The adapter 1355 includes a first lumen 1356 and a second lumen 1357. A seal member 1354 is slidingly disposed within the second lumen 1357. A resilient member 1353 is coupled to the seal member 1354 and to a first end of the adapter 1355. The first lumen 1356 is in fluid communication with the second lumen 1357. A diameter of the first lumen 1356 may taper inwardly or decrease from an outer portion toward a junction of the second lumen 1357 with the first lumen 1356, forming a small orifice or restriction of the first lumen 1356 adjacent the junction. This configuration may facilitate a pressure drop across the small orifice to allow the vacuum indicator 1370 to show that a pressure in the container 1310 is less than atmospheric pressure during a drainage procedure. Indicia may be disposed on an exterior surface of the adapter 1355 over the second lumen 1357.

The seal member 1354 can be configured to provide a seal between first and second portions 1357*a*, 1357*b* of the second lumen 1357. As detailed below, the first portion 1357*a* can be vented to or be in fluid communication with the surrounding atmosphere. The seal member 1354 may be formed of any suitable resilient material, such as silicone, latex, rubber, and thermoplastic elastomer. Other resilient materials are contemplated. The resilient member 1353 may include a linear or elongated rod shape and be formed of a resilient material equivalent to the material of the seal member 1354. In some embodiments, the seal member 1354 and the resilient member 1353 may include a unibody construct. In other embodiments, the resilient member 1353 may be a tension spring. In another embodiment, the resilient member 1353 may be a compression spring disposed in the second portion 1357*b* of the second lumen 1357. Other types of resilient members are contemplated within the scope of this disclosure.

FIG. 15A illustrates the vacuum indicator 1370 in an activated state due to a vacuum or negative gauge pressure within the container 1310. In the illustrated embodiment, the handle 1365 is rotated to expose the first and second lumens 1356, 1357 to the vacuum or negative gauge pressure within the container 1310. As set forth above, use with other types of vacuum containers or bottles is also contemplated. A pressure differential between the inside of the container 1310 and the inside of a first portion 1357*a* of the second lumen 1357 causes the seal member 1354 to be displaced toward the inlet 1342 and the resilient member 1353 to be longitudinally stretched. For instance, the inside of the first portion 1357*a* of the second lumen 1357 may be at approximately atmospheric or ambient pressure. In certain embodiments, the first portion 1357*a* is vented to or in fluid communication with atmospheric or ambient pressure. When the pressure inside of the container 1310 is less than atmospheric or ambient pressure (e.g., a vacuum or negative gauge pressure), a gas inside the first portion 1357*a* may force the seal member 1354 towards the container 1310.

FIG. 15B illustrates the vacuum indicator 1370 in an inactivated state due to depletion of the vacuum within the container 1310. As illustrated, the resilient member 1353 can draw the seal member 1354 back towards the first end of the adapter 1355 and towards the first portion 1357*a* of the second lumen 1357. The resilient member 1353 is substantially unstretched, and the pressure within the container 1310 is approximately equal to the pressure (e.g., atmospheric or ambient pressure) within the first portion 1357*a* of the second lumen 1357.

The transition of the vacuum indicator 1370 from the activated state to the inactivated state may allow the user to determine a relative level of the vacuum or negative gauge pressure within the container 1310. For example, when the seal member 1354 is in a position adjacent the inlet 1342 and the resilient member 1353 is stretched, as shown in FIG.

15A, the user may determine that the vacuum or negative gauge pressure within the container 1310 is adequate to start or continue a drainage procedure. When the seal member 1354 is positioned away from the inlet 1342 and the resilient member 1353 is unstretched, as shown in FIG. 15B, the user may determine that the vacuum or negative gauge pressure within the container 1310 is depleted or nearly depleted and is inadequate to start or continue a drainage procedure. In other words, the pressure within the container 1310 is substantially equal to the atmospheric or ambient pressure in the first portion 1357*a* of the second lumen 1357. In certain embodiments, the vacuum indicator 1370 may include an indicium, such as graduated markings, to indicate a vacuum level within the container 1310. For instance, graduated markings could be placed along the second lumen 1357.

FIGS. 16A and 16B illustrate another embodiment of a vacuum drainage collection bottle 1400. In the illustrated embodiment of FIG. 16A, the vacuum drainage collection bottle 1400 includes a container 1410 and a cap 1440 coupled to the container 1410. A vacuum indicator 1470 configured to indicate a vacuum or negative gauge pressure within the container 1410 is shown coupled to an inlet 1442 of the cap 1440. The vacuum indicator 1470 includes a T-connector 1433, a tube 1430, a seal member 1432, and a resilient member 1431. The T-connector 1433 includes a first arm 1434 and a second arm 1435. A vacuum tube 1430 is coupled to the first arm 1434 such that a lumen of the vacuum tube 1430 is in fluid communication with the container 1410. The vacuum tube 1430 can extend downwardly from the T-connector 1433 and be disposed within a groove 1436 of the container 1410 to couple the vacuum tube 1430 to the container 1410. A seal member 1432 is slidingly disposed within the lumen of the vacuum tube 1430. A resilient member 1431 is coupled to the seal member 1432 at one end and an end of the vacuum tube 1430 at an opposite end. The second arm 1435 is in fluid communication with the first arm 1434. Indicia 1437, such as tick marks or numbers to indicate a vacuum or negative gauge pressure level within the container, may be disposed on an exterior surface of the vacuum tube 1430 and/or container 1410.

The seal member 1432 can be configured to provide a seal between the first and second portions 1430*a*, 1430*b* of the vacuum tube 1430. As detailed below, the first portion 1430*a* can be vented to or be in fluid communication with the surrounding atmosphere. The seal member 1432 may be formed of any suitable resilient material, such as silicone, latex, rubber, and thermoplastic elastomer. Other resilient materials are contemplated. The resilient member 1431 may be a tension spring. In other embodiments, the resilient member 1431 may be any other type of resilient member configured to exert a tension force. In yet other embodiments, the resilient member comprises a compression spring disposed within the second portion 1430*b* of the vacuum tube 1430.

FIG. 16A illustrates the vacuum indicator 1470 in an activated state due to the vacuum or negative gauge pressure within the container 1410. The handle 1465 is rotated to expose the vacuum tube 1430 to the vacuum or negative gauge pressure within the container 1410. A pressure differential between the inside of the container 1310 and the inside of a first portion 1430*a* of the vacuum tube 1430 causes the seal member 1432 to be displaced toward the T-connector 1433 and the resilient member 1431 to be longitudinally stretched. For instance, the inside of the first portion 1430*a* of the vacuum tube 1430 may be at approximately atmospheric or ambient pressure. In certain embodiments, the first portion 1430*a* is vented to or in fluid communication with atmospheric or ambient pressure. When the pressure inside of the container 1410 is less than atmospheric or ambient pressure (e.g., a vacuum or negative gauge pressure), a gas inside the first portion 1430*a* may force the seal member 1432 towards the container 1410.

FIG. 16B illustrates the vacuum indicator 1470 in an inactivated state due to depletion of the vacuum within the container 1410. As illustrated, the resilient member 1431 can draw the seal member 1432 back towards the first portion 1430*a* of the vacuum tube 1430. The resilient member 1431 is substantially unstretched, and the pressure within the container 1410 is approximately equal to the pressure (e.g., atmospheric or ambient pressure) within the first portion 1430*a* of the vacuum tube 1430.

The transition of the vacuum indicator 1470 from the activated state to the inactivated state may allow the user to determine a relative level of the vacuum or negative gauge pressure within the container 1410. For example, when the seal member 1432 is in a position adjacent the T-connector 1433 and the resilient member 1431 is stretched, as shown in FIG. 16A, the user may determine that the vacuum or negative gauge pressure within the container 1410 is adequate to start or continue a drainage procedure. When the seal member 1432 is in the position away from the T-connector 1433 and the resilient member 1431 is unstretched, as shown in FIG. 16B, the user may determine that the vacuum or negative gauge pressure within the container 1410 is depleted or nearly depleted and is inadequate to start or continue a drainage procedure. In other words, the pressure within the container 1410 is substantially equal to the atmospheric or ambient pressure in the first portion 1430*a* of the vacuum tube 1430.

FIGS. 17A-17C illustrate another embodiment of a vacuum drainage collection bottle 1500. In the illustrated embodiment of FIG. 17A, the vacuum drainage collection bottle 1500 includes a container 1510 and a cap 1540 coupled to the container 1510. A vacuum indicator 1570 configured to indicate a vacuum or negative gauge pressure within the container 1510 is operably coupled to the cap 1540. The vacuum indicator 1570 includes a deflectable membrane 1571 coupled to the cap 1540. The deflectable membrane 1571 can be formed of any suitable elastomeric material to allow the deflectable membrane 1571 to be deflected from a convex or dome shape to a concave shape and then substantially return to the convex or dome shape. For example, the deflectable membrane 1571 can include latex, a thermoplastic elastomer, silicone, rubber, and/or natural and synthetic rubbers/elastomers, such as polyvinyl chloride, styrene, nitrile, polymer polychloroprene, and polyurethane. Other elastomeric materials are contemplated. In certain embodiments, the deflectable membrane 1571 may include a barrier coating.

FIG. 17B illustrates the vacuum indicator 1570 in an activated state where the deflectable membrane 1571 is deflected into the concave shape due to a vacuum or negative gauge pressure within the container 1510. As illustrated, the deflectable membrane 1571 is coupled to a seal ring 1572, which is coupled to a plunger 1561 of the cap 1540. The seal ring 1572 is disposed within a ring recess 1539 to retain, couple, and seal the vacuum indicator 1570 to the plunger 1561. A plunger bore 1559 is in communication with the container 1510 via a plunger channel 1574 through a proximal wall of the plunger 1561 and via a stopper channel 1573 through a distal wall of a stopper 1563. When the deflectable membrane 1571 is exposed to the vacuum or negative gauge pressure of the container 1510, the deflectable membrane 271 is deflected into the plunger bore 1559 by the pressure differential caused by the vacuum or negative gauge pressure in the container 1510.

As further shown in FIG. 17B, the deflectable membrane 1571 can be disposed adjacent to or against the opening of the plunger channel 1574 when it is in the deflected or concave configuration caused by the vacuum or negative gauge pressure in the container 1510. With the deflectable member 1571 disposed adjacent to or against the opening of the plunger channel 1574, little to no air leaks into the container 1510 via the plunger bore 1559. The deflectable membrane 1571 can also be substantially pulled against the side walls and/or bottom wall of the plunger bore 1559 to further reduce the amount of air leaking into the container 1510 via the plunger bore 1559. Minimizing or reducing the amount of air leaking into the container 1510 can increase the shelf life of the container 1510 as little vacuum is lost over time.

Additionally, the opening into the plunger channel 1574 can be relatively small. For instance, a diameter of the opening into the plunger channel 1574 can be less than about 0.06 inches, less than about 0.05 inches, less than about 0.04 inches, or less than about 0.03 inches. Stated another way, a diameter of the opening into the plunger channel 1574 can be from about 0.02 to about 0.07 inches, from about 0.02 to about 0.06 inches, from about 0.02 to about 0.05 inches, or from about 0.02 to about 0.04 inches. A relatively small opening into plunger channel 1574 can also minimize the amount of air that leaks into the container 1510 and aid in increasing the shelf life of the bottle 1500.

FIG. 17C illustrates the vacuum indicator 1570 in a non-activated state where the deflectable membrane 1571 is oriented in the convex or dome shape due to depletion of the vacuum within the container 1510. In other words, the pressure within the container 1510 is equal to or substantially equal to the atmospheric or ambient pressure outside the container 1510. As illustrated, the deflectable membrane 1571 extends upward above an upper surface of the cap 1540. The non-activated state can be due to the elasticity of the deflectable membrane 1571. In certain embodiments, the deflectable membrane 1571 must be biased towards the convex or dome orientation absent a vacuum or negative gauge pressure within the container 1510. In other embodiments, the deflectable membrane 1571 can be biased towards the convex or dome orientation absent a vacuum or negative gauge pressure within the container 1510.

The deformation or deflection of the deflectable membrane 1571 may allow a user to determine a relative level or a complete lack of the vacuum or negative gauge pressure within the container 1510. For example, when the deflectable membrane 1571 is oriented in the convex or dome shape, the user may determine that the vacuum or negative gauge pressure within the container 1510 is depleted or nearly depleted. In other words, the pressure within the container 1510 is substantially equal to the atmospheric or ambient pressure outside the container 1510. In this state, the user may not be able to either start or finish a drainage procedure. Further, when the deflectable membrane 1571 is deflected into the concave shape in the plunger bore 1559, the user may determine that there is adequate vacuum or negative gauge pressure within the container 1510 to either start or continue a drainage procedure.

Figure 18A:
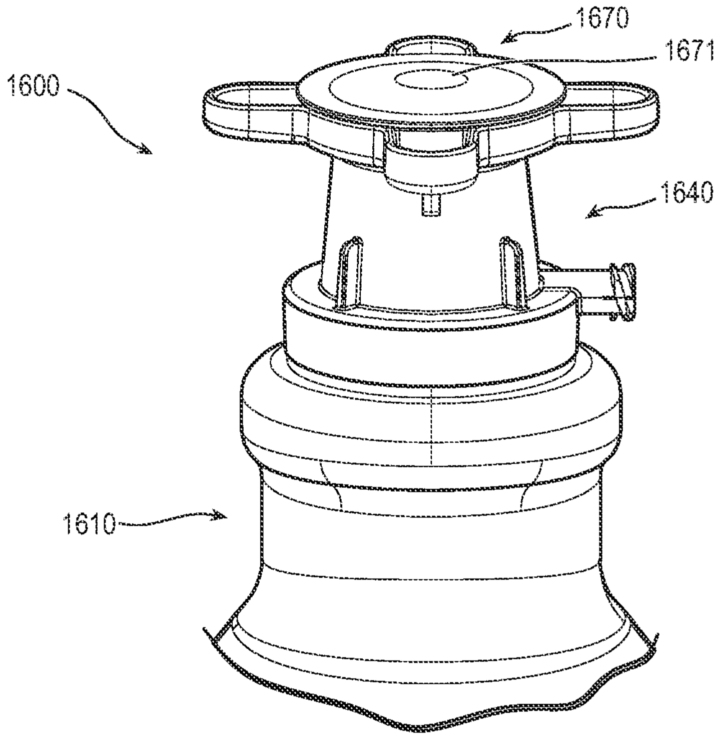
FIG. 18A is a perspective view of a portion of another embodiment of a vacuum drainage collection bottle including a deflectable member vacuum indicator.
Figure 18B:
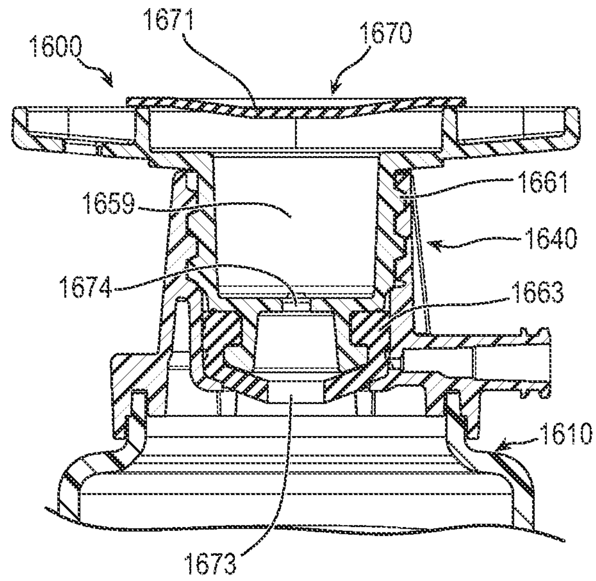
FIG. 18B is a longitudinal cross-sectional view of the portion of the vacuum drainage collection bottle of FIG. 18A with the vacuum indicator in an activated state.
Figure 18C:
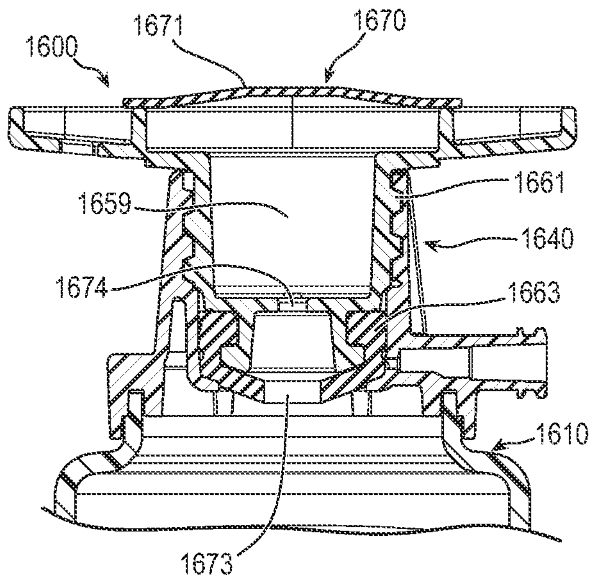
FIG. 18C is a longitudinal cross-sectional view of the portion of the vacuum drainage collection bottle of FIG. 18A with the vacuum indicator in a non-activated state.

FIGS. 18A-18C illustrate another embodiment of a vacuum drainage collection bottle 1600. In the illustrated embodiment of FIG. 18A, the vacuum drainage collection bottle 1600 includes a container 1610 and a cap 1640 coupled to the container 1610. A vacuum indicator 1670 configured to indicate a vacuum or negative gauge pressure within the container 1610 is operably coupled to the cap 1640. The vacuum indicator 1670 includes a deflectable member 1671 coupled to the cap 1640. The deflectable member 1671 can be formed of any suitable rigid material to allow a central portion of the deflectable member 1671 to be deflected from a convex shape to a concave shape and then substantially return to the convex shape. For example, in some embodiments, the deflectable member 1671 can include metal or metal alloy, such as steel, stainless steel, titanium, tin plated steel, aluminum, etc. In other embodiments, the deflectable membrane 1671 may be formed of a rigid polymer, such as polycarbonate, acrylonitrile butadiene styrene, polyvinyl chloride, or polystyrene. Other rigid materials are contemplated.

FIG. 18B illustrates the vacuum indicator 1670 in an activated state where the deflectable member 1671 is deflected into the concave shape due to a vacuum or negative gauge pressure within the container 1610. As illustrated, the deflectable member 1671 is coupled to a plunger 1661 of the cap 1640. A plunger bore 1659 is in communication with the container 1610 via a plunger channel 1674 through a distal wall of the plunger 1661 and via a stopper channel 1673 through a distal wall of a stopper 1663. When the deflectable member 1671 is exposed to the vacuum or negative gauge pressure of the container 1610, the deflectable member 1671 is deflected into or towards the plunger bore 1659 by the pressure differential caused by the vacuum or negative gauge pressure in the container 1610.

FIG. 18C illustrates the vacuum indicator 1670 in a non-activated state where the deflectable member 1671 is oriented in a convex shape due to depletion of the vacuum within the container 1610. In other words, the pressure within the container 1610 is equal to or substantially equal to the atmospheric or ambient pressure outside the container 1610. As illustrated, the deflectable member 1671 extends upward above an upper surface of the cap 1640. The non-activated state can be due to a neutral set shape of the deflectable member 1671. This neutral set shape can bias the deflectable member 1671 to the convex orientation absent a vacuum or negative gauge pressure within the container 1610.

The deformation or deflection of the deflectable member 1671 may allow a user to determine a relative level or a complete lack of the vacuum or negative gauge pressure within the container 1610. For example, when the deflectable member 1671 is oriented in the convex shape, the user may determine that the vacuum or negative gauge pressure within the container 1610 is depleted or nearly depleted. In other words, the pressure within the container 1610 is substantially equal to the atmospheric or ambient pressure outside the container 1610. In this state, the user may not be able to either start or finish a drainage procedure. Further, when the deflectable member 1671 is deflected into the concave shape into or towards the plunger bore 1659, the user may determine that there is adequate vacuum or negative gauge pressure within the container 1610 to either start or continue a drainage procedure.

In some embodiments, the deflectable member 1671 may also produce an audible indicator, such as a click or pop, when the deflectable member 1671 transitions from the activated to the non-activated state. This audible indicator can signal that the vacuum or negative gauge pressure within the container 1610 is depleted or nearly depleted. Further, when the deflectable member 1671 is in the non-activated state or convex orientation, a user may apply pressure to the deflectable member 1671 (e.g., push in with a finger) thereby causing the deflectable member 1671 to deflect inwards towards the concave orientation. Upon releasing the pressure (e.g., pulling the finger away), the deflectable member 1671 may transition back to the convex orientation and produce an audible indicator, such as a click or pop, signaling or confirming that the vacuum or negative gauge pressure within the container 1610 is depleted or nearly depleted. No such audible indicator may be produced when the deflectable member 1671 is in the activated state or concave orientation.

Figure 18D:
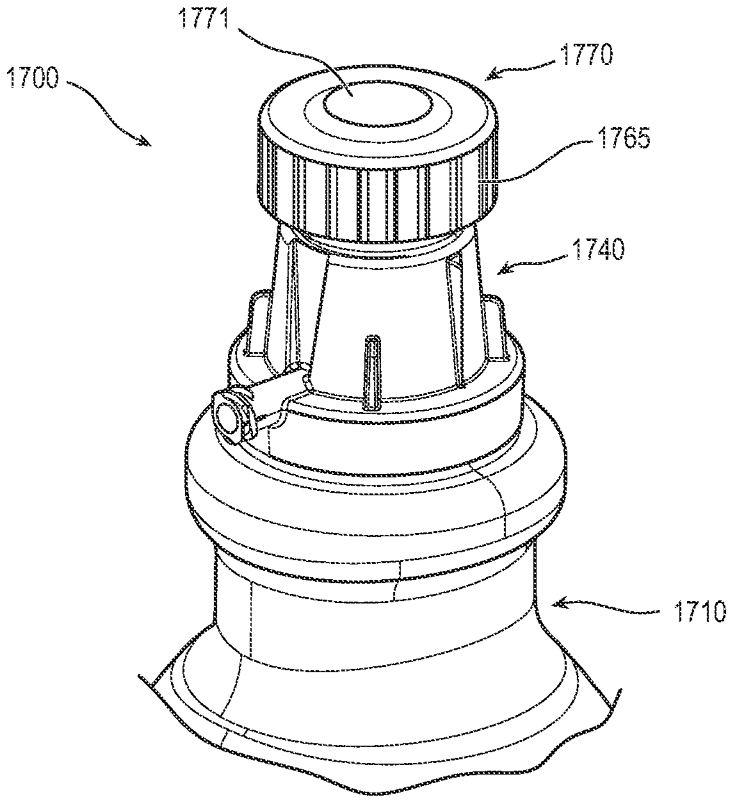
FIG. 18D is a perspective view of another embodiment of the vacuum indicator of FIG. 18A.

FIG. 18D illustrates another embodiment of the vacuum drainage collection bottle 1700. The vacuum drainage collection bottle 1700 is an alternative embodiment of the vacuum drainage collection bottle 1600 as previously described. As illustrated, the vacuum drainage collection bottle 1700 includes a cap 1740 and a container 1710. A vacuum indicator 1770, substantially similar to the vacuum indicator 1670 of FIGS. 18A-18C, is configured to indicate a vacuum or negative gauge pressure within the container 1710. This vacuum indicator 1770 is operably coupled to the cap 1740, and includes a deflectable member 1771. A handle 1765 of the cap 1740 includes a cylindrical shape. A diameter of the handle 1765 may be of any suitable dimension to allow for manipulation of the handle 1765 to close or open the cap 1740. In some embodiments, a handle having a relatively large diameter may provide a louder audible indicator than a handle having a relatively small diameter. The handle 1765 may include a plurality of ribs or other grip enhancing features, such as bumps, recesses, surface texturing, or a compliant material. Alternatively, the handle 1765 can include one or more arms or extension members as shown in FIGS. 18A-18C.

Figure 19A:
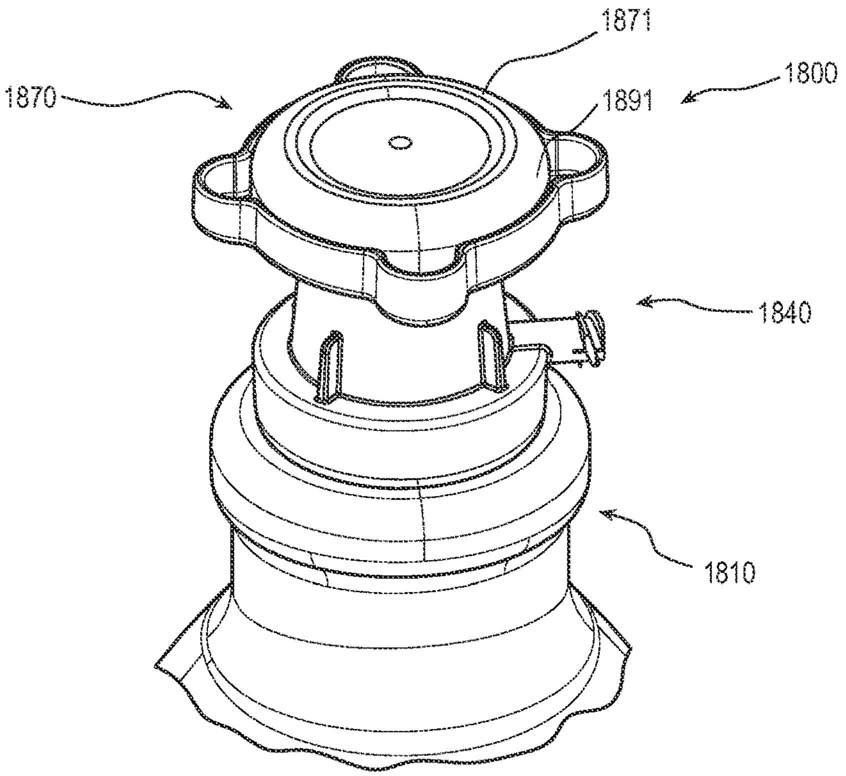
FIG. 19A is a perspective view of another embodiment of the vacuum indicator of FIG. 18A.
Figure 19B:
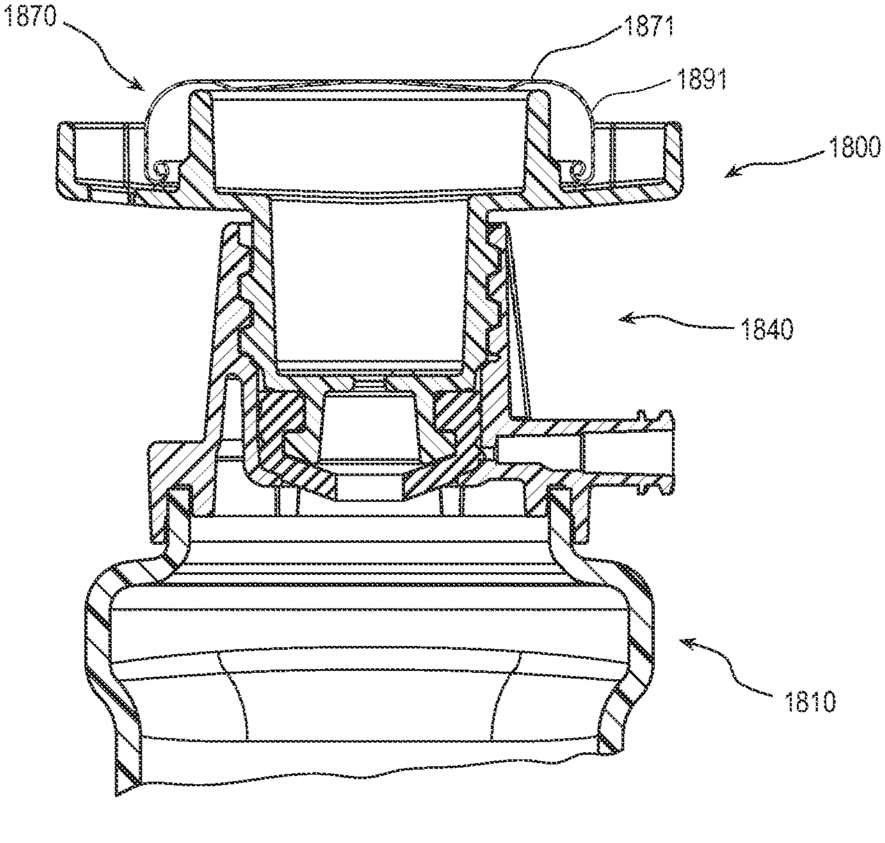
FIG. 19B is a longitudinal cross-sectional view of the vacuum indicator of FIG. 19A.

FIGS. 19A and 19B illustrate another embodiment of the vacuum drainage collection bottle 1800. The vacuum drainage collection bottle 1800 is an alternative embodiment of the vacuum drainage collection bottle 1600 as previously described. As illustrated, the vacuum drainage collection bottle 1800 includes a cap 1840 and a container 1810. A vacuum indicator 1870, substantially similar to the vacuum indicator 1670 of FIGS. 18A-18C, is configured to indicate a vacuum or negative gauge pressure within the container 1810. This vacuum indicator 1870 is operably coupled to the cap 1840 and includes a deflectable member 1871. The deflectable member 1871 includes a circumferential skirt 1891. The skirt 1891 can be configured to circumferentially surround a portion of the cap 1840 to couple the deflectable member 1871 and to provide a hermetic seal of the deflectable member 1871 to the cap 1840.

In use, any one of the disclosed vacuum drainage collection bottles may be used to drain fluid from a body cavity, such as the abdomen or the thorax, under vacuum. In some embodiments, the vacuum drainage collection bottle may be provided to the user, health care professional, or patient with a vacuum or negative gauge pressure within the vacuum drainage collection bottle. The vacuum drainage collection bottle can be disposed on a flat surface to prevent tipping. One end of a drainage tube can be coupled to an external connector of an inlet and an opposite end can be coupled to an access device (e.g., needle or catheter) disposed within the body cavity to be drained.

In certain embodiments, a handle may be rotated in a first direction to transition the vacuum drainage collection bottle from a closed state to an open state where drainage fluid flows freely into the container of the vacuum drainage collection bottle, which can be caused at least in part by the vacuum or negative gauge pressure within the vacuum drainage collection bottle. The handle can be rotated in a second direction, opposite the first direction, to transition the vacuum drainage collection bottle from the open state to the closed state.

In some embodiments, when the drainage procedure is complete, the handle may be further rotated in the first direction to remove a sealing member from the cap. When the sealing member is removed from the cap, drainage fluid collected within the container may be poured out of the container through the cap.

In certain embodiments, a status of a vacuum indicator can be observed before and/or during the drainage procedure to determine whether the vacuum or negative gauge pressure within the container is sufficient to initiate or continue the drainage procedure. In some embodiments, observing the status of the vacuum indicator can include observing the activation state of any one of an expandable vacuum indicator, an elastic membrane vacuum indicator, a linear vacuum indicator, a digital pressure sensor vacuum indicator, a retractable adapter vacuum indicator, a vacuum gauge vacuum indicator, an in-line gauge vacuum indicator, an integrated tubing vacuum indicator, a deflectable membrane vacuum indicator, and a deflectable member vacuum indicator.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of determining a vacuum within a drainage collection bottle may include one or more of the following steps: obtaining a drainage collection bottle comprising: a container; a cap; and a vacuum indicator; and observing a status of the vacuum indicator; wherein the vacuum indicator is in an activated state when the container comprises a vacuum; and wherein the vacuum indicator is in a non-activated state when the vacuum within the container is depleted. One or more additional steps can also be employed, such as actuating the cap to expose the vacuum indicator to the vacuum within the container. Other steps are also contemplated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest to the practitioner during use.

"Fluid" is used in its broadest sense, to refer to any fluid, including both liquids and gases as well as solutions, compounds, suspensions, etc., which generally behave as fluids.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

The terms "a" and "an" can be described as one, but not limited to one. For example, although the disclosure may recite a housing having "a stopper," the disclosure also contemplates that the housing can have two or more stoppers.

Unless otherwise stated, all ranges include both endpoints and all numbers between the endpoints.

Recitation in the claims of the term "first" with respect to a feature or element does not necessarily imply the existence of a second or additional such feature or element.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A drainage collection bottle, comprising:

a container comprising a vacuum;

a cap comprising a body and a sealing member, the body comprising an inlet comprising a fluid channel, the sealing member comprising a plunger, wherein the cap is coupled to the container and is configured to selectively transition the drainage collection bottle from a closed state to an open state through a rotation of the sealing member relative to the body of the cap;

wherein the sealing member is configured to vertically displace the plunger upwards and away from the container and the fluid channel upon the rotation of the sealing member to selectively transition the drainage collection bottle from the closed state to the open state; and a vacuum indicator configured to indicate the vacuum within the container, the vacuum indicator comprising a deflectable member coupled to the cap.

2. The drainage collection bottle of claim 1, wherein the vacuum indicator comprises an activated state and a non-activated state, wherein the vacuum indicator is in the activated state when the container comprises the vacuum; and wherein the vacuum indicator is in the non-activated state when the vacuum within the container is depleted.

3. The drainage collection bottle of claim 1, wherein the deflectable member comprises a deflectable membrane coupled to the cap;

wherein the deflectable membrane is deflected into the cap when the vacuum indicator is in the activated state; and wherein the deflectable membrane is dome shaped when the vacuum indicator is in the non-activated state.

4. The drainage collection bottle of claim 1, wherein the deflectable member includes a concave shape when the vacuum indicator is in the activated state; and wherein the deflectable member includes a convex shape when the vacuum indicator is in the non-activated state.

5. The drainage collection bottle of claim 4, wherein the deflectable member comprises a circumferential skirt.

6. The drainage collection bottle of claim 4, wherein the vacuum indicator is configured to produce an audible indicator when the vacuum indicator transitions from the activated state to the non-activated state.

7. A method of determining a vacuum within a drainage collection bottle, comprising:

obtaining a drainage collection bottle comprising:

a container;

a cap including a body and a sealing member, the body comprising an inlet comprising a fluid channel, the sealing member comprising a plunger, wherein the cap is configured to selectively transition the drainage collection bottle from a closed state to an open state through a rotation of the sealing member vertically displacing the plunger upwards and away from the drainage collection bottle and the fluid channel; and a vacuum indicator comprising a deflectable member coupled to the cap; and observing the status of the vacuum indicator;

wherein the vacuum indicator is in an activated state when the container comprises a vacuum; and wherein the vacuum indicator is in a non-activated state when the vacuum within the container is depleted.

8. The method of claim 7, wherein observing the status of the vacuum indicator comprises observing a position of a deflectable membrane relative to the cap.

9. The method of claim 7, wherein observing the status of the vacuum indicator comprises observing a position of a deflectable member relative to the cap.

10. The method of claim 7, wherein observing the status of the vacuum indicator comprises hearing an audible indicator.

11. A drainage collection system, comprising:
a drainage collection bottle, comprising:
a container configured to comprise a vacuum;
a cap comprising a body and a sealing member, the body comprising an inlet comprising a fluid channel, the sealing member comprising a plunger, wherein the cap is coupled to the container and is configured to selectively transition the drainage collection bottle from a closed state to an open state through a rotation of the sealing member relative to the body of the cap, the further comprising an inlet configured to attach to a drainage tube;
wherein the cap is configured to vertically displace the plunger upwards and away from the container and the fluid channel upon the rotation of the sealing member cap to selectively transition the drainage collection bottle from the closed state to the open state; and
a vacuum indicator configured to indicate the vacuum within the container, wherein the vacuum indicator comprises a rigid material disposed on the cap proximal of the inlet.

12. The drainage collection system of claim 11,
wherein the vacuum indicator comprises an activate state and a non-activated state;
wherein the vacuum indicator is in the activated state when the container comprises the vacuum; and
wherein the vacuum indicator is in the non-activated state when the vacuum within the container is depleted.

13. The drainage collection system of claim 11, wherein the vacuum indicator comprises one or more of a flexible membrane, a deflectable member, and a displaceable seal member.

14. The drainage collection bottle of claim 1, wherein:
the sealing member comprises a stopper distal to the deflectable member and having a stopper wall with a stopper channel extending therethrough;
the plunger comprises a plunger wall distal to the deflectable member and having a plunger channel extending therethrough proximal of the stopper wall and a plunger bore in communication with the container via the plunger channel and the stopper channel; and
when the deflectable member is exposed to the vacuum, the deflectable member is deflected into or towards the plunger bore.

15. The method of claim 7, wherein:
the deflectable member is deflected into or towards a plunger bore of the plunger when the vacuum indicator is in the activated state with the container comprising the vacuum; and
the deflectable member is not deflected into or towards the plunger bore when the vacuum indicator is in the non-activated state when the vacuum within the container is depleted.

16. The drainage collection system of claim 11, wherein:
the sealing member comprises:
a stopper having a stopper wall with a stopper channel extending therethrough; and
a plunger comprising a plunger wall having a plunger channel extending therethrough proximal of the stopper wall and a plunger bore in communication with the container via the plunger channel and the stopper channel; and
the vacuum indicator comprises a deflectable member that, when exposed to the vacuum, is deflected into or towards the plunger bore.

* * * * *